(12) United States Patent
Platt et al.

(10) Patent No.: US 7,893,252 B2
(45) Date of Patent: Feb. 22, 2011

(54) SELECTIVELY DEPOLYMERIZED GALACTOMANNAN POLYSACCHARIDE

(75) Inventors: David Platt, Newton, MA (US); Anatole Klyosov, Newton, MA (US)

(73) Assignee: Pro-Pharmaceuticals, Inc., Newton, MA (US)

( * ) Notice: Subject to any disclaimer, the term of this patent is extended or adjusted under 35 U.S.C. 154(b) by 0 days.

(21) Appl. No.: 12/036,608

(22) Filed: Feb. 25, 2008

(65) Prior Publication Data

US 2008/0207516 A1    Aug. 28, 2008

Related U.S. Application Data

(62) Division of application No. 10/657,508, filed on Sep. 8, 2003, now abandoned.

(51) Int. Cl.
  A61K 31/736  (2006.01)
  C08B 37/00   (2006.01)
  C12P 19/04   (2006.01)

(52) U.S. Cl. .................... 536/114; 536/123; 536/123.1; 514/54

(58) Field of Classification Search ........................ None
See application file for complete search history.

(56) References Cited

U.S. PATENT DOCUMENTS

| | | | |
|---|---|---|---|
| 3,983,140 A | 9/1976 | Endo et al. |
| 4,231,938 A | 11/1980 | Monaghan et al. |
| 4,346,227 A | 8/1982 | Terahara et al. |
| 4,444,784 A | 4/1984 | Hoffman et al. |
| 4,450,171 A | 5/1984 | Hoffman et al. |
| 4,681,893 A | 7/1987 | Roth |
| 4,739,073 A | 4/1988 | Kathawala |
| 4,804,770 A | 2/1989 | Karanewsky |
| 4,946,830 A | 8/1990 | Pulverer et al. |
| 4,970,150 A | 11/1990 | Yaku et al. |
| 5,015,632 A | 5/1991 | Nelson |
| 5,082,859 A | 1/1992 | Festal et al. |
| 5,102,888 A | 4/1992 | Fujikawa et al. |
| 5,118,673 A | 6/1992 | Carpenter et al. |
| 5,260,440 A | 11/1993 | Hirai et al. |
| 5,273,995 A | 12/1993 | Roth |
| 5,441,943 A | 8/1995 | Mcanalley et al. |
| 5,490,991 A | 2/1996 | Enriquez et al. |
| 5,498,702 A | 3/1996 | Mitchell et al. |
| 5,502,199 A | 3/1996 | Angerbauer et al. |
| 5,547,945 A | 8/1996 | Ye et al. |
| 5,569,483 A | 10/1996 | Timonen et al. |
| 5,620,961 A | 4/1997 | Markovic et al. |
| 5,626,856 A | 5/1997 | Berndt |
| 5,681,923 A | 10/1997 | Platt |
| 5,773,425 A | 6/1998 | Mcanalley et al. |
| 5,786,342 A | 7/1998 | Carpenter et al. |
| 5,831,052 A | 11/1998 | Hillman et al. |
| 5,834,442 A | 11/1998 | Raz et al. |
| 5,861,142 A | 1/1999 | Schick |
| 5,869,289 A | 2/1999 | Hawkins et al. |
| 5,891,861 A | 4/1999 | Platt |
| 5,895,784 A | 4/1999 | Raz et al. |
| 5,908,761 A | 6/1999 | Zick |
| 5,955,100 A | 9/1999 | Bosslet et al. |
| 6,190,657 B1 | 2/2001 | Pawelek et al. |
| 6,258,383 B1 | 7/2001 | Gohlke et al. |
| 6,274,566 B1 | 8/2001 | Eliaz et al. |
| 6,329,422 B1 | 12/2001 | Fischer et al. |
| 6,413,494 B1 | 7/2002 | Lee et al. |
| 6,417,173 B1 | 7/2002 | Roufa et al. |
| 6,423,314 B2 | 7/2002 | Platt |
| 6,500,807 B1 | 12/2002 | Platt et al. |
| 6,642,205 B2 | 11/2003 | Klyosov et al. |
| 6,645,946 B1 | 11/2003 | Klyosov et al. |
| 6,652,856 B2 | 11/2003 | Gotwals et al. |
| 6,680,306 B2 | 1/2004 | Chang et al. |
| 6,756,362 B2 | 6/2004 | Roufa et al. |
| 6,756,401 B2 | 6/2004 | Day et al. |
| 6,787,521 B2 | 9/2004 | Culler et al. |
| 6,844,354 B1 | 1/2005 | Iizuka et al. |
| 6,875,451 B2 | 4/2005 | Ellison et al. |
| 6,893,637 B1 | 5/2005 | Gilbertson |
| 6,912,230 B1 | 6/2005 | Salkini et al. |

(Continued)

FOREIGN PATENT DOCUMENTS

DE        19524515 A        1/1997

(Continued)

OTHER PUBLICATIONS

Avery's Drug Treatment: Principles and Practice of Clinical Pharmacology and Therapeutics, 3rd Edition, 1987, Edited by Trevor M. Speight, Chapter VIII, pp. 255-282.*

(Continued)

Primary Examiner—Eric S Olson
(74) Attorney, Agent, or Firm—Greenberg Traurig, LLP

(57) ABSTRACT

Disclosed herein are compositions and methods for treating diseases such as cancer. The compositions comprise one or more polysaccharides in an admixture with one or more therapeutic agents. This admixture can be administered to a subject in need thereof using any known method of administration. The therapeutic agent, if administered alone, can cause undesirable side-effects in the subject. The polysaccharide component minimizes or eliminates these side effects. The compositions described herein effectuate an enhanced therapeutic effect along with reduced toxicity.

12 Claims, 12 Drawing Sheets

U.S. PATENT DOCUMENTS

| | | | |
|---|---|---|---|
| 6,914,055 B2 * | 7/2005 | Klyosov et al. | 514/54 |
| 6,936,618 B2 | 8/2005 | Dormer et al. | |
| 6,964,761 B1 | 11/2005 | Condos et al. | |
| 6,982,255 B2 * | 1/2006 | Klyosov et al. | 514/54 |
| 6,986,995 B2 | 1/2006 | Rose et al. | |
| 7,012,068 B2 * | 3/2006 | Klyosov et al. | 514/54 |
| 7,166,299 B2 | 1/2007 | Yoo | |
| 2001/0026807 A1 | 10/2001 | Watts | |
| 2001/0036843 A1 | 11/2001 | Thompson | |
| 2002/0044967 A1 | 4/2002 | Yamashita et al. | |
| 2002/0058061 A1 | 5/2002 | Midha et al. | |
| 2002/0068077 A1 | 6/2002 | Klyosov et al. | |
| 2002/0107222 A1 | 8/2002 | Platt | |
| 2003/0013681 A1 | 1/2003 | Chang et al. | |
| 2004/0023925 A1 | 2/2004 | Change et al. | |
| 2004/0091503 A1 | 5/2004 | Segal et al. | |
| 2004/0254419 A1 | 12/2004 | Wang et al. | |
| 2005/0154042 A1 | 7/2005 | Bratton et al. | |
| 2005/0282773 A1 * | 12/2005 | Platt | 514/54 |
| 2006/0024357 A1 | 2/2006 | Carpenter et al. | |
| 2006/0057131 A1 | 3/2006 | Simard et al. | |
| 2006/0067927 A1 | 3/2006 | Chandrasekaran et al. | |
| 2007/0078109 A1 * | 4/2007 | Platt et al. | 514/55 |
| 2007/0258969 A1 * | 11/2007 | Zomer et al. | 424/94.6 |

FOREIGN PATENT DOCUMENTS

| | | |
|---|---|---|
| EP | 0382210 | 8/1990 |
| EP | 0595133 A | 5/1994 |
| EP | 0721784 | 7/1996 |
| EP | 0 888 776 | 1/1999 |
| EP | 0 888 776 | 7/1999 |
| GB | 2029220 | 3/1980 |
| JP | 04288017 | 10/1992 |
| JP | 05124956 | 5/1993 |
| WO | 84/04041 | 10/1984 |
| WO | WO 84/04041 | 10/1984 |
| WO | 93/08810 A1 | 5/1993 |
| WO | WO 93/08810 A1 | 5/1993 |
| WO | 96/19243 A | 6/1996 |
| WO | WO 96/19243 A | 6/1996 |
| WO | 00/04924 | 2/2000 |
| WO | WO 00/07624 | 2/2000 |
| WO | WO 00/62076 | 10/2000 |
| WO | WO 02/26262 | 4/2002 |
| WO | WO 02/057284 | 7/2002 |
| WO | WO 02/076474 | 10/2002 |
| WO | WO 03/000118 | 1/2003 |
| WO | 2004/024183 | 3/2004 |
| WO | WO 2004/024183 | 3/2004 |
| WO | 2006/017417 | 2/2006 |
| WO | WO 2006/017417 | 2/2006 |

OTHER PUBLICATIONS

2006 Chemical Abstracts Service Catalog, published by Chemical Abstracts Service, p. 52.*

Giannouli et al. "Effect of polymeric cosolutes on calcium pectinate gelation. Part 1. Galactomannans in comparison with partially depolymerised starches" Carbohydrate Polymers (2004) vol. 55 pp. 343-355.*

Palomino, E., "Carbohydrate Handles as Natural Resources in Drug Delivery", Advanced Drug Delivery Reviews, Amsterdam, NL, vol. 13, 1994, pp. 311-323.

Ouchi et al., "Synthesis and Cytotoxic Activity of Oxiodized Galactomannan/ADR Conjugate", JMS Pure Applied Chemistry, 1997, A34(6), pp. 975-989.

Katzung, Betran, Basic and Clinical Pharmacology, 1998, 7$^{th}$ Edition, Appleton & Lange, pp. 881-912.

Mey A. et al., "The Animal Lectin Galectin-3 Interacts with Bacterial Lipopolysaccharides Via Two Independent Sites", The Journal of Immunology, 1996, vol. 156, pp. 1572-1577.

Pan, Z.K. et al., "A Recombinant Listerin Monocytogenes Vaccine Expressing a Model Tumour Antigen Protects Mice Against Lethal Cell Challenges and Causes Regression of Established Tumours", Nat. Med., , 1995, vol. 1, No. 5, pp. 471-477.

Platt, D. et al, "Modulation of the Lung Colonization of B16-F1 Melanoma Cells by Citrus Pectin", Journal of National Cancer Institute, 1992, vol. 84, No. 6, pp. 438-442.

Klysov, A.A. et al, "Preclinical Studies of Anticancer Efficacy of 5-Fluorouracil When Coadministered with the 1,4-beta-D-Galactomamman", Preclinica., Sep./Oct. 2003, vol. 1, No. 4, pp. 175-183.

Platt, D. et al, "Davanat—A Modified Branched Galactomannan Enhahces Chemotherapeutics: Reflections on Manufacturing, Pre-Clinical Studies and Clinical Trials", Abstract No. 1 of papers, 227$^{th}$ ACS National Meeting, Anaheim, CA, Publisher: American Chemical Society, Washington, D.C., Mar. 28-Apr. 1, 2004.

Hetzel et al, "Different Effects of Growth Factors on Proliferation and Matrix Productions of Normal and Fibrotic Human Lung Fibroblasts", Lung, 2005, 183, pp. 225-237.

Lou et al., Pharmaceutical Research, 2002, vol. 19, pp. 396-402.

Seo et al., "Preparation of Multifunctional Low Molecular Weight Chitosan and Its Application in Cosmetics", SOFW-Journal, 128, Jan. 9, 2002, pp. 46-51.

International Search Report Mailed in Dec. 14, 2005 in connection with PCT/US2005/004430.

The Merck Manual of Diagnosis and Therapy, Seventeenth Edition, published 1999 by Merck Research Laboratories, pp. 981-995.

Oda, "Anti-Tumor Activity of Xanthan Gum" Yakuri to Chiryo, 1985, vol. 13, No. 10, pp. 5743-5750.

Van Der Boongard et al., "Successful Rescue with Leucovorin and Thymidine in a Patient with High-Dose Methotrexate Induced Acute Renal Failure", Cancer Chemotherapy and Pharmacology, 2001, vol. 47, pp. 537-540.

Jakobsen et al., "Dose-Effect Relationship of 5-Fluorouracil in the Treatment of Advanced Colorectal Cancer", Acto Oncologica, 2002, vol. 41, pp. 525-531.

2006 Chemical Abstracts Catalog, published 2005 by Chemical Abstracts Service, p. 52.

Avery' Drug Treatment: Principles and Practice of Clinical Pharmacology and Therapeutics, 3$^{rd}$ Edition, 1987, Edited by Trevor M. Speight, Chapter VIII, pp. 255-282.

International Search Report Mailed in Apr. 13, 2005 in connection with PCT/US2004/028883.

International Search Report and Written Opinion Mailed in Aug. 8, 2006 in connection with PCT/US05/27187.

Oosterveld et al, "Characterization of Arabinose and Ferulic Acid Rich Pectic Polysaccharides and Hemicelluloses from Sugar Beef Pulp", Carbohydrate Research, 200, 328, pp. 185-197, (2000).

Synthesis and Cytoxic Activity of Oxidized Galactomannan/ADR Conjugate, J.M.S. Pure Applied Chemistry, 1997, A34(6), pp. 975-989.

Lopez E, Del Pozo V, Miguel T, Sastre B, Seoane C, Civantos E, Llanes E, Baeza ML, Palomino P, Cardaba B, Gallardo S, Manzarbeitia F, Zubeldia JM, Lahoz C. Inhibition of chronic airway inflammation and remodeling by galectin-3 gene therapy in a murine model. J Iminunol. Feb. 1, 2006;176 (3): 1943-50.

Fitzner B, Walzel H, Sparmann G, Emmrich J, Liebe S, Jaster R. Galectin-1 is an inductor of pancreatic stellate cell activation. Cell Signal. Oct. 2005;17(10):1240-7. Epub Jan. 21, 2005.

Maeda N, Kawada N, Seki S, Arakawa T, Ikeda K, Iwao H, Okuyama H, Hirabayashi J, Kasai K, Yoshizato K. Stimulation of proliferation of rat hepatic stellate cells by galectin-1 and galectin-3 through different intracellular signaling pathways. J Biol Chem. May 23, 2003;278(21):18938-44. Epub Mar. 19, 2003.

Yamazaki K, Kawai A, Kawaguchi M, Hibino Y, Li F, Sasahara M, Tsukada K, Hiraga K. Simultaneous induction of galectin-3 phosphorylated on tyrosine residue, p21(WAF1/Cipl/Sdil), and the proliferating cell nuclear antigen at a distinctive period of repair of hepatocytes injured by CC14. Biochem Biophys Res Commun. Feb. 2, 2001;280(4):1077-84.

Wang L, Friess H, Zhu Z, Frigeri L, Zimmermann A, Korc M, Berberat PO, Buchler MW. Galectin-1 and galectin-3 in chronic pancreatitis. Lab Invest. Aug. 2000;80(8):1233-4 I.

Kasper M, Hughes RC. Immunocytochemical evidence for a modulation of galectin 3 (Mac-2), a carbohydrate binding protein, in pulmonary fibrosis. J Pathol. Jul. 1996;179(3):309-16.

Wert, Susan, Mitsuhiro Yoshida, Ann Marie LeVine, Machiko Ikegami, Tracy Jones. Gary F. Ross, James H. Fisher, Thomas R. Korfhagen, and Jeffrey A. Whitsett, Increased metalloproteinase activity, oxidant production, and emphysema in surfactant protein D gene-inactivated mice. PNAS, May 2000; 97: 5972-5977.

Brown, Michael, et al., A Receptor-Mediated Pathway for Cholesterol Homeostasis. Nobel Lecture, Dec. 9, 1985.

Endo A. The discovery and development of HMG-CoA reductase inhibitors. J. Lipid Research, 33, 1992, 1569-1582.

Endo A. Compactin (ML-236B) and related compounds as potential cholesterol-lowering agents that inhibit HMG-CoA reductase. J. Med. Chem., 28, No. 4, 401-405, 1985.

Endo A., Kuroda M., and Tanzawa K. Competitive inhibition of 3-hydroxy-3-methylglutaryl coenzyme A reductase by ML-236A and ML-236B, fungal metabolites, having hypocholesterolemic activity. FEBS Letters, 72, 323-326, 1976.

Holgate G.A., Ward W.H.J., and McTaggart F. Molecular mechanism for inhibition of 3-hydroxy3-methylglutaryl CoA (HMG-CoA) reductase by rosuvastatin. Biochem. Soc. Transactions, 31, Part 3, 528-531, 2003.

Endo A., Kuroda M, and Tsujita Y. ML-236A, Ml-236B, and ML-236C, new inhibitors of cholesterogenesis produced by *Penicillium citrinum*. J. Antibiot. (Japan), 29, 1346-1348, 1976.

HMG-CoA Reductase Inhibitors. General Monograph, Canadian Pharmacists Association, 2002.

Weber C., Erl W., Weber K.S.C., and Weber P.C. HMG-CoA reductase inhibitors decrease CD11 b expression and CD11b-dependent adhesion of monocytes to endothelium and reduce increased adhesiveness of monocytes isolated from patients with hypercholesterolemia. J. Am. Coll. Cardiol., 30, 1212-1217, 1997.

Desager J.P., Normans Y. Clinical pharmacokinetics of 3-hydroxy-3-methylglutaryl-coenzyme A reductase inhibitors. Clin. Pharmacokinetics, 31, 348-371, 1996.

Bellosta S., Via D., Canavesi M., Pfister P., Fumagalli R., and Paoletti R. HMG-CoA reductase inhibitors reduce MMP-9 secretion by macrophages. Arterioscler. Thromb. Vasc. Biol., 18, 1671-1678, 1998.

Akira K., Amano M., Okajima F., Hashimoto T., and Oikawa S. Inhibitory effects of amlodipine and fluvastatin on the deposition of advanced glycation end products in aortic wall of cholesterol and fructose-fed rabbits. Biol. Pharm. Bull. 29, No. 1, 75-81, 2006.

Bernick C., Katz R., Smith N.L., Rapp S., Bhadelia R., Carlson M., Kuller L. Statins and cognitive function in the elderly. Neurology, 65, 1388-1394, 2005.

Masse I., Bordet R., Deplanque D., Al Khedr A., Richard F., Libersa C., and Pasquier F. Lipid lowering agents are associated with a slower cognitive decline in Alzheimer's disease. J. Neurology, Neurosurgery, and Psychiatry. 76, 1624-1629, 2005.

Miida T., Takahashi A., Tanabe, N., Ikeuchi, T. Can statin therapy really reduce the risk of Alzheimer's disease and slow its progression? Current Opinion in Lipidology. 16, No. 6, 619623, 2005.

Barlogie, B. et al., "Etoposide, Dexamethasone, Cytarabine, and Cisplatin in Vincristine, Doxorubicin, and Dexamethasone-Refactory Myeloma", Journal of Clinical Oncology, vol. 7, No. 10 (1989).

Belka, C. et al. "Sensitization of resistant lymphoma cells to irradiation-induced apoptosis by the death ligand TRAIL." Oncogene 20, 2190-2196 (2001).

Bergenheim, A.T. et al. "Uptake and retention of estramustine and the presence of estramustine binding protein in malignant brain tumours in humans." Br. J. Cancer 67, 358‾361 (1993).

Bianco, C. et al. "Enhancement of Antitumor Activity of Ionizing Radiation by Combined Treatment with the Selective Epidermal Growth Factor Receptor-Tyrosine Kinase Inhibitor." Clin. Cancer Res. 8, 3250-3258 (Oct. 2002).

Bonavida, B. et al. "Selectivity of TRAIL-mediated apoptosis of cancer cells and synergy with drugs: The trail to non-toxic cancer therapies (Review)." Int. J. Oncol. 15, 793-802 (Oct. 1999).

Chauhan et al., "A Novel Carbohydrate-Based Therapeutic GCS-100 Overcomes Bortezomib Resistance and Enhances Dexamethasone-Induced Apoptosis in Multiple Myeloma Cells." Cancer Res, 65: (18), (2005).

Christodoulou et al. "Anti-proliferate activity and mechanism of action of titanocene dichloride." Br. J. Cancer 77(12), 2088-2097 (1998).

Citro et al. "c-myc Antisense Oligodeoxynucleotides Enhance the Efficacy of Cisplatin in Melanoma Chemotherapy in Vitro and in Nude Mice." Cancer Res. 58, 283-289 (Jan. 15, 1998).

Comicueret, 0. "Linkingcyclins to transcriptional control." Gene 299, 35-55 (2002).

Elez, R. et al. "Tumor regression by combination antisense therapy against Plk1 and Bcl-2." Oncogene 22, 69-80 (2003).

Hershberger, P.A. "Calcitriol (1,25-Dihydroxycholecalciferol) Enhances Paclitaxel Antitumor Activity in Vitro and in Vivo and Accelerates Paclitaxel-induced Apoptosis." Clin. Cancer Res. 7, 1043-1051 (Apr. 2001).

Imam et al. "Interferon-Alpha Induces bcl-2 Proto-Oncogene in Patients with Neuroendocrine Gut Tumor Responding to its Antitumor Action." Anticancer Res. 17, 4659-4666 (1997).

Liu et al., "Citrus Pectin: Characterization and Inhibitory Effect on Fibroblast Growth Factor-Receptor Interaction." J. Agric. Food Chem. 49:3051-3057 (2001).

Miller et al. "Phase II Trial of Docetaxel and Vinorelbine in Patients with Advanced Non-Small Cell Lun. Cancer." J. Clin. Oncol. 18 6 , 1346-1350 (Mar. 2000).

Mizutani et al. "Enhanced sensitivity of bladder cancer cells to tumor necrosis factor related apoptosis inducing ligand mediated apoptosis by cisplatin and carboplatin." J. Urology 165, 263-270 (Jan. 2001).

Mohammad et al. "The Addition of Brysostatin 1 to Cycolphosphamide, Doxorubicin, Vincristine, and Prednisone (CHOP) Chemotherapy Improves Response in a CHOP-resistent Human Diffuse Large Cell Lymphoma Xenograft Model." Clin. Cancer Res. 6, 4950-4956 (Dec. 2000).

Swannie, H. C. et al. "Protein Kinase C Inhibitors." Curr. Oncol. Reports 4(1), 37-46 (Jan. 2002).

Tu, Y. et al., Upregulated Expression of BCL-2 in Multiple Myeloma Cells Induced by Exposure to Doxorubicin, Etoposide, and Hydrogen peroxide Blood, vol. 88, No. 5, 1805-1812 (1996).

Warfield, P. R. "Adhesion of Human Breast Carcinoma to Extracellular Matrix Proteins Is Modulated by Galectin-3." Invasion Metastasis 17, 101-112 (1998).

Aparicio, A. "In vitro cytoreductive effects on multiple myeloma cells induced by bisphosphonates." Leukemia 12, 220-229 (1998).

Baldus, S.E. et al. "Increased Galactin-3 Expression in Gastric Cancer: Correlations with Histopathological Subtypes, Galactosylated Antigens and Tumor Cell Proliferation." Tumor Biol. 21, 258-266 (Jul. 2, 1999).

Berberat, P.O. et al. "Comparative Analysis of Galectins in Primary Tumors and Tumor Metastasis in Human Pancreatic Cancer." J. Histochem. Cytoochem. 49, 539-549 (2001).

Bold, R.J. et al. "Chemosensitization of Pancreatic Cancer by Inhibition of the 26S Proteasome." J. Surg. Res. 100, 11-17 (2001).

Brewer, C.F. "Binding and cross-linking properties of galectins. Biochim. Biophys." Acta 1572, 255-262 (2002).

Burke, P.A. et al. "Combined Modality Radioimmunotherapy." Cancer 94, 1320-1331 (Feb. 15, 2002).

Camby, I. et al. "Galectins are differently expressed in supratentorial pilocytic astrocytomas, astrocytomas, anaplastic astrocytomas and glioblastomas, and significantly modulate tumor astrocyte migration." Brain Pathology 11, 12-26 (2001).

Cherayil, B.J. et al. "Molecular cloning of a human macrophage lectin specific for galactose." PNAS 87, 7324-7328 Sep. 1990).

Choufani, G. et al. "The Levels of Expression of Galectin-1, Galectin-3, and the Thomsen‾Friedenreich Antigen and Their Binding Sites Decrease as Clinical Aggressiveness Increases in Head and Neck Cancers. Cancer 86, 2353-2363 (Dec. 1, 1999)."

Cindolo, L. et al. "Galectin-1 and Galectin-3 Expression in Human Bladder Transitional-Cell Carcinomas." Int. J. Cancer 84, 39-43 (1999).

Cooper, D.N.W. "Galectinomics: finding themes in complexity." Biochim Biophys Acta 1572, 209-231 (2002).

Coqueret, O. "Linking cyclins to transcriptional control." Gene 299, 35-55 (2002).

Cotter, F.E. "Controlling the Mitochondria! Gatekeeper for Effective Chemotherapy." British Journal of Haematology 111:52-60 (2000).

Danguy, A. et al. "Galectins and cancer." Biochim. Biophys Acta 1572, 285-293 (2002).

Definition of apoptosis and cytotoxicity, Wikipedia, (2007).

Del Bino, G. et al. "Altered Susceptibility of Differentiating HL-60 Cells to Apoptosis Induced by Antitumor Drugs." Leukemia 8, 281-288 (Feb. 1994).

Dipaola, R.S. and Aisner, J. "Overcoming bcl 2-and p53 Mediated Resistance in Prostate Cancer." Seminars in Oncology 26, 112-116 (Feb. 1999).

Eastman, A. and Rigas, J.R. "Modulation of Apoptosis Signaling Pathways and Cell Cycle Regulation." Seminars in Oncology 26, (Oct. 7-16, 1999).

Fan, W. et al. "In vitro evaluation of combination chemotherapy against human tumor cells." Oncology Reports 5, 1035-1042 (1998).

Francois, C. et al. "Galectin-1 and Galectin-3 Binding Pattern Expression in Renal Cell Carcinomas." Am. J. Clin. Pathol. 112, 194-203 (1999).

GBC 590 SafeScience Clinical Data. R&D Focus Drug News, DRUGNL. an:1186 (2001).

Glinsky, V.V. et al. "Effects of Thomsen-Friedenreich Antigen-specific Peptide P-30 on B–Galactoside-mediated Homotypic Aggregation and Adhesion to the Endothelium of MDA-MB 435 Human Breast Carcinoma Cells." Cancer Res. 60, 2584-2588 (May 15, 2000).

Glinsky, V.V. et al. "The Role of Thomsen-Friedenreich Antigen in Adhesion of Human Breast and Prostate Cancer Cells to the Endothelium." Cancer Res. 61, 4851 4857 (Jun. 15, 2001).

Gong, H.C. et al. "The NH2 Terminus of Galectin-3 Governs Cellular Compartmentalization and Functions in Cancer Cells." Cancer Res. 59, 6239-6245 (Dec. 15, 1999).

Grant, S. and Dent, P. "Rational integration of agents directed at novel therapeutic targets into combination chemotherapeutic regiments." Curr. Opin. Investigational Drugs 2, 1600-1605 (2001).

Hara, I. et al. "Sodium butyrate induces apoptosis in human renal cell carcinoma cells and synergistically enhances their sensitivity to anti-Fas-mediated cytotoxicity." Int. J. Oncol. 17, 1213-1218 (2000).

Hernandez, J.D. and Baum, L.G. "Ah, sweet mystery of death! Galectins and control of cell fate." Glycobiology 12, 127R-136R (2002).

Hortobagyi, G.N. "Recent Progress in the Clinical Development of Docetaxel (Taxotere)." Seminars in Oncology 26, 32-36 (Jun. 1999).

Hrdlickova, E. et al. Detection of galectin-3 in tear fluid at disease states and immunohistochemical and lectin histochemical analysis in human corneal and conjunctival Ophthalmol. 85, 1336-1340 (2001).

Inohara, H. et al. "Expression of Galectin-3 in Fine-Needle Aspirates as a Diagnostic Marker Differentiating Benign from Malignant Thyroid Neoplasms." Cancer 85, 2475-2484 (Jun. 1, 1999).

Inufusa, H. et al. "Role of galectin-3 in adenocarcinoma liver metastasis." Int. J. Oncol. 19, 913-919 (2001).

Lurisci, I. et al., "Concentrations of Galectin-3 in the Sera of Normal Controls and Cancer Patients," Clinical Cancer Research 6:1389-1393 (2000).

Jensen-Jarolim, E. et al. "Anti-Galectin-3 IgG Autoantibodies in Patients with Crohn's Disease Characterized by Means of Phage Display Peptide Libraries." J. Clin. Immunol. 21(5), 348–356 (2001).

Johnson, K. R. et al. "Antagonistic Interplay between Antimitotic and G1-S Arresting Agents Observed in Experimental Combination Therapy." Clin. Cancer Res. 5, 2559-2565 (Sep. 1999).

Juliao, S. et al. "Galectin-3: A Marker and Diagnostic Aid for Chordoma." Present at the 47th Annual Meeting, Orthopaedic Research Society, p. 0846, Feb. 25-28, 2001, San Francisco, CA.

Karmanos, Barbara Ann Cancer Institute. "Novel Therapeutic Targets &Therapies." www.karmanos.orq/we/research/prostate/novel.html retrieved on Jan. 27, 2003.

Kilpatrick, D. C. "Animal Lectins: a historical introduction and overview." Biochim. et Biophys..'I Acta 1572, 187-197 (2002).

Kim, Hyeong-Reh Choi et al., "Cell Cycle Arrest and Inhibition of Anoikis by Galectin-3 in Human Breast Epithelial Cells," Cancer Research 59:4148-4154 (1999).

Kim, R. et al. "A pitfall in the survival benefit of adjustment chemotherapy for node and hormone receptor-positive patients with breast cancer: The paradoxical role of Bcl-2 oncoprotein (Review)." Int. J. Oncol. 19, 1075-1080 (2001).

Klass, R. J. et al. "Eradication of Human Non Hodgkin's Lymphoma in SCID Mice by BCL 2 Antisense Oligonucleotides Combine with Low-Does Cyclophosphamide." Clin. Cancer Res. 6, 2492 2500 (Jun. 2000).

Leffler, H. et al. "Specificity of Binding of Three Soluble Rat Lung Lectins to Substituted and Unsubstituted Mammalian B Galactosides." J. Biol. Chem. 261(22), 10119-10126 (Aug. 5, 1986).

Lim, Y. et al. "Identification of autoantibodies associated with systemic lupus erythematosus. Biochem." Biophys. Res. Comm. 295, 119-124 (2002).

Lin, H.M. et al., "Galectin-3 Mediates Genistein-induced G2/M Arrest and Inhibits Apoptosis," Carcinogenesis 21(11):1941-1945 (2000).

Linehan, W. M. "Inhibition of Prostate Cancer Metastasis: a Critical Challenge Ahead. J. Nat." Cancer Inst. 87(5), 331-332 (Mar. 1, 1995).

Liu, F.-T. et al. "Intracellular functions of galectins." Biochim et Biophys Acta 1572, 263-273 (2002).

Lopes De Menezes, D. E. et al. "Molecular and Pharmacokinetic Properties Associated with the Therapeutics of BcI-2 Antisense Oligonucleotide G3139 Combined with Free and Liposomal Doxorubicin." Clin. Cancer Res. 6, 2891-2902 (Jul. 2002).

Lotz, M. M. et al. "Decreased expression of Mac-2 (carbohydrate binding protein 35) and loss of its nuclear localization are associated with the neoplastic progression of colon carcinoma." PNAS 90, 3466-3470 Aid (1993).

Majlessipour, F. "The Combination Regimen of Idarubicin and Taxotere is Effective Against Human Drug-resistant Leukemic Cell Lines." Anticancer Res. 22, 1361-1368 (2002).

Matarrese P., et al., (Abstract) "Galectin-3 Overexpression Protects from Apoptosis by Improving Cell Adhesion Properties," Int. Cancer 85(4):545-554 (2000).

Matarrese, P., et al. "Galectin-3 overexpression protects from cell damage and death by influencing mitochondrial homeostasis." FEBS Letters 473, 311-315 (2000).

Mazurek et al., "Phosphorylation of the B-Galactoside-binding Protein Galectin-3 Modulates Binding to its Ligands," The Journal of Biological Chemistry 275(46):36311-36315 (2000).

Mey, A. et al. "Expression of the galactose binding protein Mac-2 by human melanoma cell-lines." Cancer Letters 81, 155-163 (1994).

Nakamura, M. et al. "Involvement of galectin-3 expression in colorectal cancer progression and metastasis." Int. J. Oncol. 15, 143-148 (1999).

Ohannesian, D. W. et al. "Carcinoembryonic Antigen and Other Glycoconjugates Act as Ligands for Galectin-3 in Human Colon Carcinoma Cells." Cancer Res. 55, 2191-2199 (May 15, 1995).

Oncolink: Lilly Oncology Treatment Options. www.oncolink.com/treatment/section.cfm retrieved on Feb. 12, 2003.

Orlandi, F. et al. "Galectin 3 Is a Presurgical Marker of Human Thyroid Carcinoma." Cancer Res. 58, 3015 3020 (Jul. 15, 1998).

Perillo, N. L. Galectins: versatile modulators of cell adhesion, cell proliferation, and cell (1998).

Pienta, K.J. et al. "Inhibition of spontaneous metastasis in a rat prostate cancer model by oral administration of modified citrus pectin." J. Nat. Cancer Inst. 87(5), 348-353 (Mar. 1, 1995).

Pugliese, G. "The Diabetic Milieu Modulates the Advanced Glycation End Product Receptor Comples in the Mesangium by Inducing or Upregulating Galectin-3 Expression." Diabetes 49, 1249 1257 (Jul. 2000).

Rabinovich, G.A. "Role of galectins in inflammatory and immunomodulatory processes. Biochim. Biophys." Acta 1572, 274-284 (2002).

Rabinovich, G.A. et al. "Recombinant Galectin-1 and Its Genetic Delivery Suppress Collagen-induced Arthritis via T Cell Apoptosis." J. Exp. Med. 190(3), 385-397 (Aug. 2, 1999).

Rabinovich, G.A. et al. "The antimetastatic effect of a single low dose of cycolphosphamide involves modulation of galectin-1 and Bcl-2 express." Cancer Immunol. Immunother. 50, 597 (2002).

Rabinovich, G.A. et al., "Galectins and Their Ligands: Amplifiers, Silencers or Tuners of the InflammatoryResponse?" Trends in Immunology 23(6):313-320 (2002).

Raynaud, F. I. "Pharmacokinetics of G3139, a Phosphorothioate Oligodeoxynucleotide Antisense to bcl-2, after Intravenous Administration or Continuous Subcutaneous Infusion to Mice." J. Pharmacol Exp. Therapeutics 281(1), 420-427 (1997).

Rudin, C. M. et al. "A pilot trial of G3139, a bcl-2 antisense oligonucleotide, and paclitaxel in patients with chemorefracto111 small cell lung cancer." Ann. Oncol. 13, 539-545 (2002).

Ruiter, G.A. et al. "Alkyl-Lysophospholipids as Anticanger Agents and Enhancers of Radiation-Induced Apoptosis." Int. J. Radiation Oncol. Biol. Phys. 49(2), 415-419 (2001).

Sano, H. et al. "Human Galectin-3 Is a Novel Chemoattractant for Monocytes and Macrophages." J. Immunol. 165, 2156-2164 (2000).

Sauer, G. et al. "New Molecular Targets of Breast Cancer Therapy." Strahlenther. Onkol. 178(3), 123-133 (2002).

Shih, C. et al. "Cryptophycins: A Novel Class of Potent Antimitotic Antitumor Depsipeptides." Curr. Pharm. Des. 7, 1259-1276 (2001).

Sörme, P. et al. "Low Micromolar Inhibitors of Galectin-3 Based on 3-Derivatization of N Acet Ilactosmaine." ChemBioChem 3, 183-189 (2002).

Takahashi, T. et al. "Mechanisms of the apoptotic activity of CI-F-araA in a human T-ALL cell line, CCRF-CEM." Cancer Chemother Pharmacol. 50, 193-201 (2002).

Tentori, L. et al. "Role of Wild-Type p 53 on the Antineoplastic Activity of Temozolomide Alone or Combined with Inhibitors of Poly(ADP-Ribose) Polymerase." J. Pharmacol. Exp. Therapeutics 285(2), 884-893 (1998).

Tortora, G. et al. "Combined Blockade of Protein Kinase A and Bcl-2 by Antisense Strategy Induces Apoptosis and Inhibits Tumor Growth and Angiogenesis." Clin. Cancer Res. 7, 2537 2544 (Aug. 2001).

Tortora, G. et al. "Protein Kinase A as Target for Novel Integrated Strategies of Cancer Therapy." Ann. N.Y. Acad. Sci. 968, 139-147 (2002).

Tu, S.-M. et al. "Combination adriamycin and suramin induces apoptosis in bcl-2 expressing prostate carcinoma cells." Cancer Letters 93, 147-155 (1995).

Usuda, J. et al. "Increased Cytotoxic Effects of Photodynamic Therapy in IL-6 Gene Transfected Cells via Enhanced Apoptosis." Int. J. Cancer 93, 475-40 (2001).

Vivat-Hannah, V. et al. "Synergistic Cytotoxicity Exhibited by Combination Treatment of Selective Retinoid Ligands with Taxol (Paclitaxel)." Cancer Res. 61(24), 8703-8711 (Dec. 15, 2001).

Webster's New World Dictionary, 3rd. ed., Simon & Schuster (New York, 1988) p. 433.

Xia, F. "The molecular basis of radiosensitivity and chemosensitivity in the treatment of breast cancer." Semin. Radiat. Oncol. 12(4), 296-304 (2002).

Xu, X.-C. et al. "Differential expression of galectin-1 and galectin-3 in benign and malignant salivary gland neoplasms." Int. J. Oncol. 17, 271-276 (2000).

Yamamoto, D. et al. "Synergistic action of apoptosis induced by eicosapentaenoic acid and TNP-470 on human breast cancer cells." Breast Cancer Res. Treatment 55, 149-160 (1999).

Yamaoka, K. et al. "Overexpression of A fl-Galactoside Binding Protein Causes Transformation of BaIb3T3 Fibroblast Cells." Biochem. Biophys. Res. Comm. 179(1), 272-279 (Aug. 30, 1991).

Yang, R.-Y. et al. "Expression of galectin-3 modulates T-cell growth and apoptosis." PNAS 93, 6737-6742 (Jun. 1996).

Yoshii, T. et al. "Galectin-3 Phosphorylation is Required for Its Anti-apoptotic Function and Cell Cycle Arrest." J. Biol. Chem. 277(9), 6852-6857 (Mar. 1, 2002).

Zeng, S. et al. "In Vitro Evaluation of Schedule-dependent Interactions between Docetaxel and Doxorubicin against Human Breast and Ovarian Cancer Cell." Clin. Cancer Res. 6, 3766-3773 (Sep. 2000).

Zetter, "Angiogenesis and tumor metastasis," Annu. Rv. Med. 49:407-424 (1998).

Zhu, W.-Q. et al. Rapid Release of Intracellular Galectin-3 from Breast Carcinoma Cells by Fetuin. Cancer Res. 61, 1869-1873 (Mar. 1, 2001).

Non-Final Office Action from United States Patent and Trademark Office for U.S. Appl. No. 10/557,120 dated Nov. 20, 2007.

Final Office Action from United States Patent and Trademark Office for U.S. Appl. No. 10/557,120 dated Aug. 28, 2008.

Non-Final Office Action from United States Patent and Trademark Office for U.S. Appl. No. 10/108,237 dated Oct. 4, 2004.

Non-Final Office Action from United States Patent and Trademark Office for U.S. Appl. No. 10/649,131 dated Oct. 4, 2004.

Non-Final Office Action from United States Patent and Trademark Office for U.S. Appl. No. 10/597,930 dated Nov. 30, 2007.

Final Office Action from United States Patent and Trademark Office for U.S. Appl. No. 10/597,930 dated Dec. 23, 2008.

Non-Final Office Action from United States Patent and Trademark Office for U.S. Appl. No. 10/649,130 dated Oct. 4, 2004.

Non-Final Office Action from United States Patent and Trademark Office for U.S. Appl. No. 10/889,555 dated Dec. 29, 2008.

Non-Final Office Action from United States Patent and Trademark Office for U.S. Appl. No. 11/182,096 dated Sep. 3, 2008.

Final Office Action from United States Patent and Trademark Office for U.S. Appl. No. 10/657,508 dated Jul. 18, 2008.

Non-Final Office Action from United States Patent and Trademark Office for U.S. Appl. No. 10/657,508 dated Aug. 23, 2007.

Non-Final Office Action from United States Patent and Trademark Office for U.S. Appl. No. 10/657,508 dated Oct. 2, 2006.

Non-Final Office Action from United States Patent and Trademark Office for U.S. Appl. No. 09/961,681 dated Feb. 26, 2002.

Final Office Action from United States Patent and Trademark Office for U.S. Appl. No. 09/961,681 dated Sep. 9, 2002.

Non-Final Office Action from United States Patent and Trademark Office for U.S. Appl. No. 09/818,596 dated Jun. 2, 2003.

Non-Final Office Action from United States Patent and Trademark Office for U.S. Appl. No. 09/818,596 dated Dec. 19, 2002.

* cited by examiner

US 7,893,252 B2

SELECTIVELY DEPOLYMERIZED GALACTOMANNAN POLYSACCHARIDE

RELATED APPLICATION

This application is a divisional and claims the priority of U.S. application Ser. No. 10/657,508, filed Sep. 8, 2003, now abandoned the entirety of which is incorporated herein by reference.

FIELD OF THE INVENTION

The present invention, relates to compositions and methods for treating disease. Specifically, the instant invention relates to compositions comprising a polysaccharide and pharmaceutical agent, wherein the polysaccharide lowers the toxicity profile of the drug as well as increase its efficacy.

BACKGROUND OF THE INVENTION

The most widely used methods to treat cancer are surgery, radiation and chemotherapy. Cancer patients often receive a combination of these treatments and about half of all patients receive chemotherapy. Unfortunately, chemotherapeutic agents have significant limitations relating to their toxic effect on the patient and the efficacy of a particular dosage to target and kill tumor cells.

Most chemotherapeutic agents kill cancer cells once they begin to undergo division and replication. Cells are killed by disrupting cell division. For example, a chemotherapeutic agent may prevent the formation of new DNA or block some other essential function within a cell. Some chemotherapeutic agents may work by inducing apoptosis, essentially causing the cells to commit suicide by triggering the cells' programmed death process. Although these agents are effective for treating cancer cells that generally grow rapidly through unregulated cell division, they also kill healthy non-cancerous cells as they undergo ordinary cell division. This toxic effect is particularly apparent in fast-growing normal cells, such as bone marrow cells, those in the digestive tract, hair follicles, and reproductive cells. Because chemotherapy harms healthy tissue, the effectiveness of a drug is limited by its dosage levels and treatment frequency such that it should not exceed the tolerance levels for non-cancerous cells. Moreover, the chemotherapy regimen often dramatically diminishes the quality of a patient's life through its physical and emotional side effects. Without the ability to target the drug exclusively to cancerous tissue, chemotherapy dosages must be kept within a range (i.e., the therapeutic index) that healthy tissue can tolerate, thus often reducing the optimal effectiveness of chemotherapy on diseased tissue.

If the toxicity of chemotherapeutic agents could be reduced, then practitioners would be able to increase the dosage of a drug without the resultant unacceptable side effects. Increasing efficacy in a drug can be translated into a decreased dosage of drug, which again minimizes the potential harmful effects on a patient while offering maximum benefit. Decreasing dosage by increasing efficacy of a chemotherapeutic drug together with a reduction in toxic side effects would lead to improvement of the patient's quality of life through controlling the tumor and through reducing harmful side effects.

To date there have been various approaches to balancing effectiveness of chemotherapy treatment with the harmful side effects. For example, some approaches involve spreading out the chemotherapy treatments by giving smaller doses more frequently in order to help a patient better tolerate the treatment. Other approaches include adding additional substances to the chemotherapy regime. Such substances include those that putatively combat the noxious side effects (such as nausea) of the chemotherapeutic agents and allow the chemotherapy drug to be better tolerated by the patient. Such substances can also allow higher doses of drug to be used to combat the cancer because the patient's tolerance of the chemotherapeutic agent can be improved or increased.

Despite the advances that have been made in chemotherapeutic regimens, there remains a significant unmet medical need for increasing the efficacy of chemotherapeutic agents while at the same time reducing their toxicity. There is a need for therapies to more effectively combat cancer yet at the same time provide patients with a better quality of life during treatment by reducing the harmful and debilitating side effects of most chemotherapeutic treatments.

SUMMARY OF THE INVENTION

The present invention comprises compositions and methods for treating disease, such as cancer. The compositions of the present invention comprise one or more polysaccharides together with one or more pharmaceutical agents. The methods of the instant invention comprise the co-administration of one or more pharmacological agents and one or more polysaccharides to a subject in need thereof, wherein the pharmaceutical preparation including the pharmacological agent and polysaccharide has reduced toxicity. In one aspect, the compositions of the present invention has both reduced toxicity and increase efficacy.

In one embodiment of the present invention, a method is described for treating cancer in a subject comprising administering to the subject a mixture of one or more polysaccharides and an effective dose of a chemotherapeutic agent in a pharmaceutically acceptable formulation, wherein the polysaccharide is selected from group consisting of galactomannans, which are available from a number of plant and microbial sources. This pharmaceutical formulation is then administered to a patient in need thereof in an acceptable manner well known to those skilled in the art.

In another embodiment of the present invention, a mixture of one or more polysaccharides and one or more chemotherapeutic agents is administered to a subject in need thereof, wherein the mixture comprises a sufficient amount of polysaccharide and chemotherapeutic agent in a ratio suitable for reducing the toxic side-effects in a subject while being effective against a particular pathology being treated, wherein the polysaccharide is selected from group consisting of galactomannans (from *Cyamopsis tetragonolobus*), Arabinogalactan (from *Larix occidentalis*), Rhamnogalacturonan (from potato), Carrageenan (from *Eucheuma* Seaweed), and the Locust Bean Gum (from *Ceratonia siliqua*). The toxic side-effects being defined as those physiological effects (symptoms) realized by the subject resulting from the administration of the chemotherapeutic agent absent the polysaccharide.

In another embodiment of the present invention, a pharmaceutical formulation is provided that includes a mixture of one or more polysaccharides and an effective dose of one or more chemotherapeutic agents in a pharmaceutically acceptable formulation, wherein the polysaccharide is selected from group consisting of galactomannans (from *Cyamopsis tetragonolobus*), Arabinogalactan (from *Larix occidentalis*), Rhamnogalacturonan (from potato), Carrageenan (from *Eucheuma* Seaweed), and the Locust Bean Gum (from *Ceratonia siliqua*). In one aspect, the mixture in the formulation contains an amount of one or more polysaccharides and one or more chemotherapeutic agents in a ratio suitable for reducing any toxic side-effect in the subject. The polysaccharide to chemotherapy ratio could be in the range from 10:1 up to 1:10. With the 50,000 MW modified galactomannan the optimum ratio was in the range from 6:1 to 1:3. In another aspect, the mixture contains an amount of one or more polysaccharides and one or more chemotherapeutic agents in a ratio suitable for enhancing efficacy of chemotherapeutic effect for treating the cancer. In yet another aspect, the mixture contains an amount of one or more polysaccharides and one or more chemotherapeutic agents in a ratio suitable for effectively treating cancer as well as reducing any potential toxic side-effect(s). In still a further aspect of the invention, a method is provided for treating cancer in a subject in need thereof that includes administrating an a mixture of one or more polysaccharides and an effective dose of one or more chemotherapeutic agents formulated so that the chemotherapeutic agent has enhanced therapeutic efficacy in the presence of the polysaccharide component.

The following terms shall have the meanings indicated below, unless the context otherwise requires.

"Subject" refers to an animal including a mammal, such as human, dog, cat, pig, cow, sheep, goat, horse, rat, mouse, and alike.

"Patient" refers to a human subject who has presented in a clinical setting with a particular symptom or symptoms consistent with a pathophysiological process.

"Polysaccharide" refers to polymers comprised primarily of monomers of one or more sugars and substituted sugars. The sugar monomers can be modified in ways well known to those in the art.

"Efficacy" for a toxic therapeutic agent refers to the relationship between a minimum effective dose and the accompanying toxic side-effects. Efficacy of an agent is increased if a therapeutic end point can be achieved by administration of a lower dose or a shorter dosage regimen. If toxicity can be decreased, a therapeutic agent can be administered on a longer dosage regimen or even chronically with greater patient compliance and improved quality of life. Further, decreased toxicity of an agent enables the practitioner to increase the dosage to achieve the therapeutic endpoint sooner, or to achieve a higher therapeutic endpoint. "Efficacy" for a non-toxic therapeutic agent relates to improved therapeutic effect for treating a condition.

"Pharmaceutically acceptable carrier" refers to any and all solvents, dispersion media, e.g., human albumin or cross-linked gelatin polypeptides, coatings, antibacterial and antifungal agents, isotonic, e.g. sodium chloride or sodium glutamate, and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidural administration, (e.g., by injection or infusion). Depending upon the route of administration, the active compound can be coated in a material to protect the compound from the action of acids and other natural conditions that can inactivate the compound.

"Active Compound" refers to any and all chemotherapeutic agents used herein for the treatment of cancer, and any and all added agents that increase efficacy of the chemotherapeutic agent and/or decrease toxicity of the chemotherapeutic agent.

"Parenteral Administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

"Toxic" refers to any adverse effect caused by an agent when administered to a subject.

"Tumor Regression" was scored (excluding nonspecific deaths) as "partial" (less than 50 percent of its size at the beginning of the treatment), or "complete" (tumor becomes unpalpable).

"Duration of Regression" refers to the interval during which a tumor classified as a partial or complete regression continues to be below 50 percent of its size at first treatment.

"Evaluation Size" refers to the tumor mass selected at one or two mass doubling versus beginning with the initial tumor size at the start of treatment.

"Time Required for Tumor Mass Doubling" is the time to reach the evaluation size, it is used in the calculations of the overall delay in the growth of the median tumor [(T–C)/C× 100%], where T–C (days) is the difference in the median of times postimplant for tumors of the treated (T) groups to attain an evaluation size compared to the median of the control (C) group. The T–C value is measured excluding nonspecific deaths, and any other animal that dies whose tumor failed to attain the evaluation size.

"Effective Dose" is that dose of chemotherapeutic agent required to achieve a predetermined physiological effect, such as tumor size reduction, while not exceeding a patient's tolerance for the agent.

"Enhanced therapeutic efficacy" means that the therapeutic index of chemotherapeutic agent (alone or as a composition comprising one or more polysaccharides and one or more therapeutic agents) exceeds the desired physiological effect, such as tumor size reduction, tumor growth delay, etc., compared to that of a reference chemotherapeutic agent, and/or improving a patient's tolerance for the agent.

DETAILED DESCRIPTION

Figure 1:
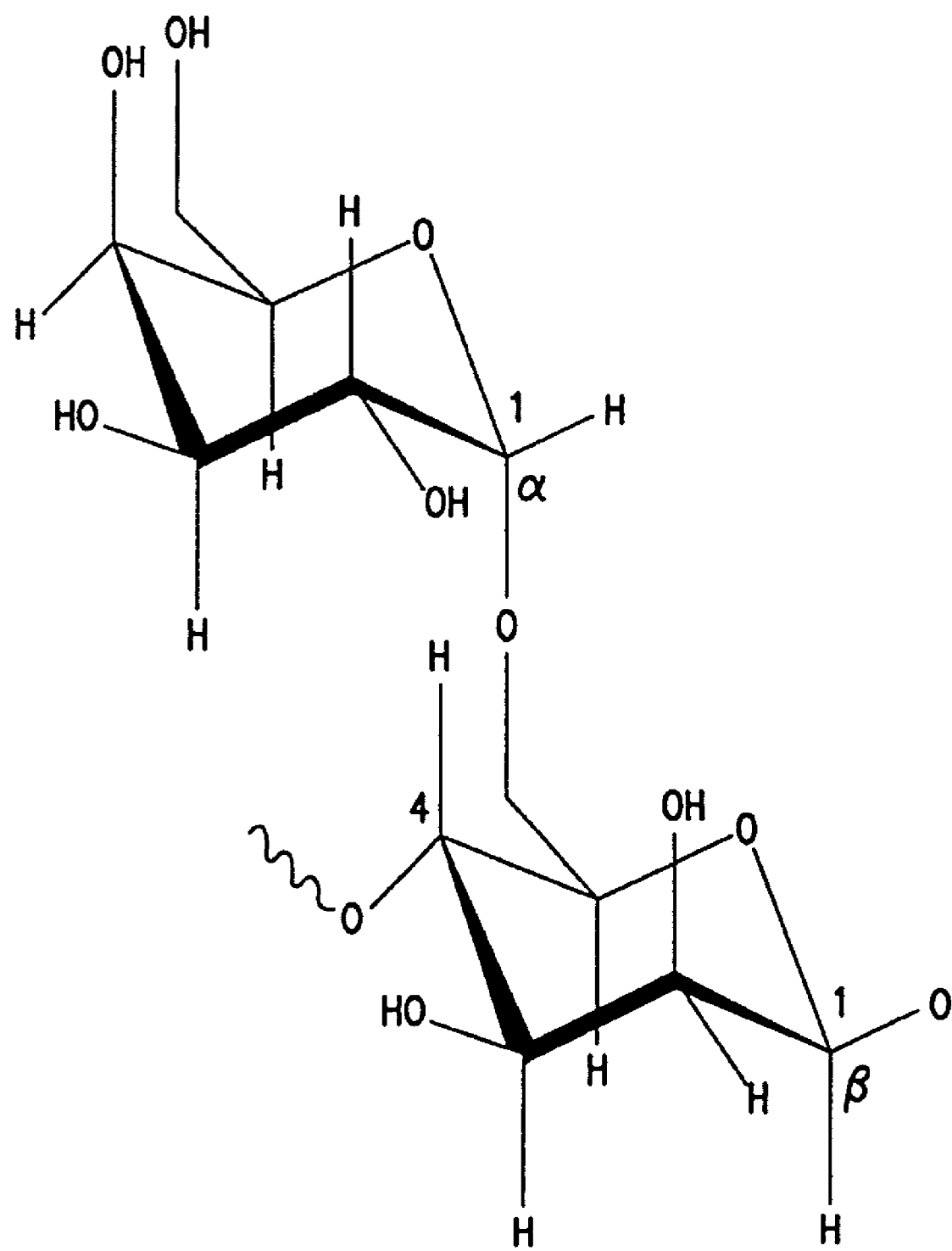
FIG. 1 is the stereochemical configuration of galactomannan.

The present invention provides compositions and methods for treating an individual in need thereof. The compositions of the invention comprise a mixture of one or more polysaccharides and one or more therapeutic agents. The compositions of the present invention are directed toward individuals afflicted with a disease, such as cancer. The polysaccharide/therapeutic agent compositions of the present invention, once administered to an individual in need thereof, preferably enhance the therapeutic efficacy of the therapeutic agent while concomitantly reduce its toxic side-effects.

The most widely used methods to treat cancer are surgery, radiation and chemotherapy. Cancer patients often receive a combination of these treatments and about half of all patients receive chemotherapy. Unfortunately, chemotherapeutic agents have significant limitations relating to their toxic effect on the patient and the efficacy of a particular dosage to target and kill tumor cells.

Because chemotherapy harms healthy tissue, the effectiveness of a drug is limited by its dosage levels and treatment frequency such that it should not exceed the tolerance levels for non-cancerous cells. Moreover, the chemotherapy regimen often dramatically diminishes the quality of a patient's life through its physical and emotional side effects. Without the ability to target the drug exclusively to cancerous tissue, chemotherapy dosages must be kept within a range (i.e., the therapeutic index) that healthy tissue can tolerate, thus reducing the optimal effectiveness of chemotherapy on diseased tissue. Therefore, if the toxicity of chemotherapeutic agents can be reduced, practitioners would be able to increase the dosage of drug without the resultant toxic side effects.

One class of drugs, fluoropyrimidines (e.g., 5-fluorouracil (5-FU)), have been used for over forty years in standard chemotherapy regimens for a number of solid tumors including colorectal, breast, non-small cell carcinoma of the lung (NSCCL), gastric, pancreatic, ovarian and head and neck tumors. Schedule modification of 5-FU administration including prolonged intravenous infusion, and pharmacokinetic modulation has produced improved response rates and tolerability, however, this has not always translated well into improved survival rates. There remains an opportunity to develop agents which, when given with 5-FU, enhance tumor specific delivery, and improve safety and convenience of administration such as what is described herein.

5-FU has been the mainstay for therapy of cancers like colorectal cancer for the last two decades. Colorectal adenocarcinoma is the second leading cause of cancer deaths accounting for 10-12 percent of the total number. An estimated 130,000-155,000 new cases occur yearly in the United States. Approximately 25% of patients present with distant metastases, and an additional 20% develop metastases during their lifetime. The mortality rate in 1990 was $24/100,000$ for males and $16/100,000$ for females. Although survival from this disease has improved by approximately 8% over the past two decades largely due to earlier detection.

Advances in the treatment of advanced colorectal cancer are largely attributed to modifications of, or additions to, regimens centered around 5-FU which remains the first line chemotherapeutic agent for the treatment of metastatic colorectal cancer. Bolus intravenous ("IV") therapy, which was the standard of care until approximately a decade ago, produced response rates ranging from 11% to 18%. The intensity of exposure to 5-FU as measured by the area under the "concentration vs. time curve" correlates well not only with anti-tumor activity but also with toxicity. Regimens which include five days of treatment every three weeks produce mucositis, diarrhea and neutropenia. Regimens aimed at enhancing the duration of thymidylate synthase inhibition by continuous IV infusion or bolus injection in combination with leucovorin (folinic acid) have improved response rates ranging from 22% to 38%. Continuous infusion regimens can result in hand-foot syndrome in approximately 20% of patients, mucositis is similar in continuous infusion compared with bolus therapy, but diarrhea and neutropenia are less frequent by the continuous infusion route.

Topoisomerase I inhibitors such as irinotecan have been used in patients with advanced colorectal cancer who are chemotherapy naive or who have failed 5-FU regimens. In chemotherapy naive patients, a Phase II study by the Southern Italy Oncology Group showed an 18% response rate in patients receiving 5-FU plus leucovorin, and a 40% response rate in patients receiving irinotecan given just prior to 5-FU plus leucovorin. Grade 3-4 toxicity was uncommon in both treatment arms. In patients who have failed 5-FU, two randomized trials showed that irinotecan improved response rates and survival when compared to best supportive care or continuous infusion 5-FU. Irinotecan produces more severe life-threatening myelosuppression and diarrhea than 5-FU. The overlapping toxicities of these two agents also limits the use of both compounds together at maximal dose intensity.

Oxaliplatin is a diaminocyclohexane platinum complex which has been shown to have a single agent response rate of 10% in previously treated colorectal cancer patients. When combined with 5-FU infusions in patients receiving initial therapy, response rates as high as 58% have been observed. Complications of this drug include peripheral neuropathy and oral-pharyngeal dysesthesias. Clinical trials are currently underway to compare oxaliplatin combinations with 5-FU or irinotecan to 5-FU as initial treatments for advanced colorectal cancer.

The present invention provides methods and compositions for combining one or more polysaccharides with one or more therapeutic agents for treating disease in a subject. The methods of the invention include administering an effective dose of a mixture of one or more polysaccharides together with an effective dose of one or more therapeutic agents such that a mixture is formulated wherein the therapeutic agent has enhanced therapeutic efficacy and decreased toxicity in the presence of the polysaccharide.

One disease targeted by the present invention is cancer. The types of cancer envisaged to be within the scope of the present invention include, but not limited to, chronic leukemia, breast cancer, sarcoma, ovarian carcinoma, rectal cancer, throat cancer, melanoma, colon cancer, bladder cancer, lung cancer, mammary adenocarcinoma, gastrointestinal cancer, stomach cancer, prostate cancer, pancreatic cancer, and Kaposi's sarcoma.

However, other treatment regimes are envisaged to be within the scope of this invention include, but not limited to, anti-depressants, anti-inflammatory agents, gastroenterology drugs (for treating ulcers and associated disorders), anti-psychotic drugs, anti-hyperlipidemic agents, etc., as many therapeutic agents must be administered as a chronic medicine, i.e., on a long-term basis, potential reduction in dosage and improvement in quality of life become significant factors in availability, cost of therapeutic agents, and patient compliance.

The effective dose of the polysaccharide component is that amount needed to minimize or completely mitigate some, if not all, of the toxic side-effects experienced by a subject receiving a chemotherapeutic agent. In one aspect, the effective dose is that amount needed to enhance the efficacy of the therapeutic agent. In another aspect, the effective dose is that amount need to minimize or eliminate the toxic sides effects of a drug as well as increase the drug's efficacy in treating a subject.

Enhanced therapeutic efficacy means that the therapeutic index of chemotherapeutic agent (as a composition comprising one or more polysaccharides and exceeds the desired physiological effect, such as tumor size reduction, tumor growth delay, etc.,) compared to that of a reference chemotherapeutic agent, or/and improving a patient's tolerance for the chemotherapeutic agent.

In one embodiment, a composition comprising one or more polysaccharides and one or more therapeutic agents is disclosed. The polysaccharides are formed from monomeric units. Modified polysaccharides are also considered to be within the scope of the present invention and can include modification by, for example, limited controlled depolymerization, or, for example, having lipid, protein, or nucleic acid moieties affixed to the monomeric units of the polysaccharide. The polysaccharide of the composition can be branched or unbranched. The polysaccharides include, but not limited to, galactomannans available from a number of plant and microbial sources. e.g., plants: *Gleditsia triacanthos, medicago falcate, Cyamopsis tetragonoloba, Trigonella Foenumgraecum* and microbial like *Ceratonia siliqua Xanthomonas campestris*, yeast and mold galactomannan, Arabinogalactan (from *Larix occidentalis*), Rhamnogalacturonan (from potato), Carrageenan (from *Eucheuma* Seaweed), and the Locust Bean Gum (from *Ceratonia siliqua*. In one aspect, the polysaccharide can be β-1,4-D-galactomannan and include a ratio of mannose to galactose in the range of about 1.7. In another aspect, the molecular weight of the galactomannan polysaccharide is in the range of about 4,000 to about 200,000 D. In a particular aspect, the galactomannan has an average weight of about 40,000 to 60,000 D. In another aspect, the structure of the galactomannans is a poly-β-1,4 mannan backbone, with side substituents affixed via a-1-6-glycoside linkages. In one aspect, the galactomannan polysaccharide can be β-1,4-D-galactomannan. In one particular aspect, the polysaccharide is (((1,4)-linked (β-D-mannopyranose)17-((1,6)-linked-(β-D-galactopyranose)10)12). In another aspect, the galactomannan can be a derivative of Guar gum from seeds of *Cyamopsis tetragonoloba.*

The polysaccharides of the present invention can have side branches of target specific carbohydrates, such as, galactose, rhamnose, mannose, or arabinose which provides the surface of a polymer recognition capabilities in targeting specific lectin type receptors on the surface of cells, especially tumor cells. Branches can be a single unit or two or more units of oligosaccharide.

The compositions of the present invention can further include an enhancer. An example of such an enhancer is leucovorin. Studies have shown that the addition of enhancers such as leucovorin have improved response rates. See, Benson, A. B., Oncology, 12 (10 suppl 7):28-34, 1998; Ardalan, B., et al., Cancer Invest., 16:293-294, 1998; and Harms, B. A., et al., Chapter 62 in Clinical Oncology, 2nd ed., Abeloff (ed), 2000, Churchill Livingstone, Inc. pp. 1611-1637, the entire teaching of which is incorporated herein by reference. In chemotherapy naïve patients, a Phase II study conducted by the Southern Italy Oncology Group showed an 18% response rate in patients receiving 5-FU plus leucovorin, and a 40% response rate in patients receiving irinotecan given just prior to 5-FU plus leucovorin. See, Maiello, E., et al., Ann. Oncol. 11: 1045-51, 2000, the entire teaching of which is incorporated herein by reference.

The therapeutic agent of the present composition includes all known pharmaceuticals listed in, for example, the Physicians Desk Reference, as well as experimental therapeutic agents. In one aspect, the therapeutic agents are chemotherapeutic agents.

The modern era of cancer chemotherapy began after World War II with the introduction of nitrogen mustard, an alkylating agent developed for clinical use as a consequence of the hematopoietic toxicity encountered with sulfur mustard and aminopterin, a folate antagonist. These compounds produced dramatic remissions in patients with lymphoma and in children with acute lymphocytic leukemia. Unfortunately, cures were not obtained because of the rapid development of drug resistance, a problem that has been noted with single agent treatment of each new drug introduced into the clinic.

Studies in experimental tumors have clearly established that optimal antitumor effects occur when dosages used are the highest achievable, consistent with host tolerance, which is the subject of the present invention. In more recent years the term dosage intensity has been employed to define the amount of drug delivered per unit time, usually in milligrams per square meter per week. For certain drugs, such as alkylating agents that are not very schedule dependent, dose intensity delivered directly relates to treatment outcome. In most tumors in which cure is possible, this issue becomes critical and less than optimal dosing may result in treatment failure.

In many human tumors that are curable by combination chemotherapy, there is a certain subset of patients, usually with advanced, bulky tumors, that are not effectively treated by these programs. The possibility of curing even this subset of patients by increasing dose intensity using autologous marrow rescue or hemotopoietic growth factors continues to be investigated.

Drug resistance occurs rapidly when treatment with a single drug is used. A combination of chemotherapeutic agents can be used to treat various cancers. Drugs can be used in combination when the dose-limiting toxicity of one drug is nonoverlapping with the other. When toxicity occurs, it may be difficult to adjust subsequent drug doses, because the major offending agent may not be known.

Cycle-active agents are drugs that require a cell to be in cycle, i.e., actively going through the cell cycle preparatory to cell division to be cytotoxic. Some of these drugs are effective primarily against cells in one of the phases of the cell. The importance of this designation is that cell cycle-active agents are usually schedule-dependent, and that duration of exposure is as important and usually more important than dose. In contrast, noncell cycle-active agents are usually not schedule-dependent, and effects depend on the total dose administered, regardless of the schedule. Alkylating agents are generally considered to be noncycle active, whereas antimetabolites are prototypes of cycle-active compounds.

An example of cell cycle-active agents are fluoropyrimidines, such as 5-fluorouracil (5-FU) and 5-fluorodeoxyuridine (5-FUdR). 5-FU exerts its cytotoxic effects by inhibition of DNA synthesis, or by incorporation into RNA, thus inhibiting RNA processing and function. The active metabolite, of 5-FU that inhibits DNA synthesis through potent inhibition of thymidylate synthase is 5-fluorodeoxyuridylate (5-FdUMP). In rapidly growing tumors, inhibition of thymidylate synthetase appears to be the key mechanism of cell death caused by 5-FU; however, in other tumors, cell death is better correlated with incorporation of 5-FU into RNA. Incorporation of 5-FU into DNA can occur also and may contribute to 5-FU cytotoxicity.

5-FU and 5-FUdR have antitumor activity against several solid tumors, most notably colon cancer, breast cancer, and head and neck cancer. A preparation containing 5-FU is used topically to treat skin hyperkeratosis and superficial basal cell carcinomas.

The major limiting toxicities of 5-FU and 5-FUdR include marrow and GI toxicity. Stomatitis and diarrhea usually occur 4-7 days after treatment. Further treatment is usually withheld until recovery from the toxic side-effects occurs. The nadir of leukopenia and of thrombocytopenia usually occurs 7-10 days after a single dose of a 5-day course. The dose-limiting toxicity to infusions of 5-FUdR through the hepatic artery is transient liver toxicity, occasionally resulting in biliary sclerosis. Less common toxicities noted with 5-FU after systemic administration are skin rash, cerebellar symptoms and conjunctivitis.

Another example of a cell cycle-active agent is methotrexate. This folate antagonist was one of the first antimetabolites shown to induce complete remission in children with ALL. Methotrexate (amethopterin) and aminopterin are analogs of the vitamin folic acid. Methotrexate, and similar compounds, acts by inhibiting the enzyme dihydrofolate reductase. As a consequence of this inhibition, intracellular folate coenzymes are rapidly depleted. These coenzymes are required for thymidylate biosynthesis as well as purine biosynthesis, as such, DNA synthesis is blocked by the use of methotrexate and alike. There is considerable toxicity associated with the use of methotrexate such as myelosuppression and GI distress. An early sign of methotrexate toxicity to the GI tract is mucositis. Severe toxicity can result in diarrhea that is due to small bowel damage that can progress to ulceration and bleeding.

Cytosine, arabinoside (ara-C) is an antimetabolite analog of deoxycytidine. In the analog, the OH group is in the β configuration at the 2' position. This compound was first isolated from the sponge Cryptothethya crypta. Ara-C is the drug of choice for the treatment of acute myelocytic leukemia. Ara-C is converted intracellularly to the nucleotide of triphosphate (ara-CTP) that is both an inhibitor of DNA polymerase and incorporated into DNA. The latter event is considered to cause the lethal action of ara-C. Nausea and vomiting are observed with patients being treated with ara-C.

There are many other chemotherapeutics considered to be within the scope of this invention. Purine analogs, such as 6-mercaptopurine and 6-thioguanine, define drugs that are also employed as a cure against cancer. Hydroxyurea is another drug that is used to treat cancer. Hydroxyurea inhibits ribonucleotide reductase, the enzyme that converts ribonucleotides at the diphosphate level to deoxyribonucleotides. Vinca alkaloids are also involved in the treatment of cancer. The vinca alkaloids include vinblastine, vincristinei and vindesine. Epipodophyllotoxin is a derivative of podophyllotoxin that is used in the treatment of such cancers as leukemia, Hodgkin's, and other cancers.

Alkylating agents such as mechlorethamine, phenylalanine mustard, chlorambucil, ethylenimines and methyl melamines, and alkylsulfonates are employed to treat various cancers.

Nitrosoureas like carmustine, lomustine, and streptozocin are used to treat various cancers and have the ability to readily cross the blood-brain barrier.

Cisplatin (diamino-dichloro-platinum) is a platinum coordination complex that has a broad spectrum antitumor activity. Cisplatin is a reactive molecule and is able to form inter- and intrastrand links with DNA in order to cross-link proteins with the DNA. Carboplatin is another platinum based antitumor drug.

Triazenes like dacarbazine and procarbazine are a part of the antitumor arsenal.

There are antibiotics that have antitumor activity such as anthracyclines, such as doxorubicin, daunorubicin, and mitoxantrone. Other antitumor antibiotics include bleomycin, dactinomycin, mitomycin C, and plycamycin.

There are ether antitumor drugs, like asparaginase, that are considered to be within the scope of this invention. These and the other drugs mentioned above all have a toxicity profile that is well known to those skilled in the art.

Other therapeutic agents that can be used in the present invention include cyclophosphamide (cytoxan), melphalan (alkeran), chlorambucil (leukeran), carmustine (BCNU), thiotepa, busulfan (myleran); glucocorticoids such as prednisone/prednisolone, triamcinolone (vetalog); other inhibitors of protein/DNA/RNA synthesis such as dacarbazine (DTIC), procarbazine (matulane); and paclitaxel.

Examples of therapeutic agents that may be administered with one or more polysaccharides to reduce their toxicity or enhance efficacy include the following: anti-infectives including antibiotics, anti-virals and vaccines, antineoplastics, cardiovascular drugs including antiarrythmics, antihypertensives, etc., central nervous system drugs including analgesics, anorectics, anticonvulsants, anti-inflammatories and tranquilizers, etc. OTICS, opthalmics, gastrointestinal including anti-ulcer drugs, anticholinergic drugs etc., hormones, respiratory drugs including allergy medications, bronchodilators and decongestants, topical drugs and vitamins and minerals.

Without wishing to be bound by theory, there are three possible mechanisms that may account for the beneficial effect of a polysaccharide like galactomannan in a mixture with a therapeutic drug such as 5-FU. One involves a direct physical interaction between the drug and galactomannan. For example, galactomannan may increase cancer cell membrane fluidity and permeability as a result of galactose-specific interactions at the surface of the target cell. The polysaccharide can thus serve as an effective vehicle for delivery of the drug to the target. Additionally, galactomannan may act to inhibit aggregation of tumor cells and their adhesion to normal cells so that the cancer fails to metastasize. Once the polymer-drug conjugate enters the tumor, which the polysaccharide recognizes by virtue of its structure and composition, the polysaccharide may release the anti-cancer drug. The toxicity of a therapeutic agent may be reduced because the drug is inactive as long as it is bound to the polymer. Once the polymer-drug conjugate enters the tumor, the polysaccharide may release therapeutic agent.

Another possible mode of action for the polysaccharide like galactomannan may involve its interaction with some regulatory sites in a biological system, for example, if those sites are governed by galactose-specific residues, such as galectins. Yet another possible mode of action may involve an inhibitory effect of the polysaccharide having a certain chemical structure (a certain Man:Gal ratio) and a certain size (molecular weight) on enzymatic systems responsible for a rapid clearance of therapeutic agent from the body, and therefore may potentially increase the bioavailability and prolong the mean residence time of drug in the body, thus improving the therapeutic profile of a drug in cancer therapy.

In one particular aspect, the polysaccharide is galactomannan. Use of a galactomannan-containing composition can have an immediate effect of increasing the responses of patients to chemotherapy. For example, one effect is a decrease in the dosage of the therapeutic agent required for effective chemotherapy. It can have an immediate beneficial effect for the patient by decreasing toxicity of the chemotherapeutic agent, as here exemplified, but not limited to, adramycin, 5-FU, irinotecan and cisplatin.

Galactomannan can be obtained from a variety of natural sources such as plants and microbial sources. The polysaccharide can also be synthetically made. Galactomannan can be derived from carob gum (*Ceratonia siliqua*), guar gum (*Cyamopsis tetragonoloba*), and honey locust (*Gleditsia triacanthos*), are examples of commercial available galactomannans.

Galactomannan is a polymer comprising mannose and galactose. The resulting ratio of mannose to galactose in the isolated polysaccharide can vary according to the source of the galactomannan and the isolation procedure used, typically ranging between one and four.

The polysaccharide galactomannan is a polymer that can occur in a variety of size ranges. For example, galactomannan can have a molecular weight in the range of about 20,000 to about 600,000 D. The galactomannan can range in size from about 90,000 to about 415,000 D. Moreover, the galactomannan can be derivatized or hydrolyzed resulting in fragments of the native molecule for example in the range of 4,000 to 60,000.

In one embodiment of the present invention, a method is disclosed for treating a disease, such as cancer, comprising administering to the subject a mixture of one or more polysaccharides and an effective dose of one or more chemotherapeutic agents in a pharmaceutically acceptable formulation, wherein the polysaccharide is selected from group consisting of galactomannans from various sources. This pharmaceutical formulation is then administered to a patient in need thereof in any acceptable manner known in the art. In one aspect of this embodiment, the components, i.e., the polysaccharide and pharmaceutical, can be administered separately to a subject.

The polysaccharide component of this embodiment can be prepared using methods articulated herein. If for example galactomannan is one of the components for the present embodiment, it can be extracted from Guar gum which itself is obtained from seeds of the *Cyamopsis tetragonoloba*.

Once the polysaccharide is prepared it can be stored as a powder or as an aqueous solution, for example, in physiological saline. Other acceptable physiological solutions can be used as well. A pharmaceutical preparation can be formed using the prepared polysaccharide and one or more pharmaceutical agents. The polysaccharide theraputic' IV dose can be in the range of 10 to 200 mg/kg and is usually optimized to the optimal therapeutic dose of the chemotherapeutic agent for best therapeutic performance. For 5-FU the optimum dose (in mice) has been established at 30 to 150 mg/kg with best results at about 120 mg/kg. However, it could vary with other chemotherapy. The pharmaceutical carriers that can be used for the administration of the present composition are well known to those skilled in the art.

The routes of administration include oral, intravenous, subcutaneous, intraperitoneal, intramuscular, and alike. The route of administration can be any route sufficient to introduce the composition into a subject in a manner consistent with good medical practice. These various routes of administration are well known to those skilled in the art.

In another embodiment of the present invention, a mixture of one or more polysaccharides and chemotherapeutic agent is administered to a subject in need thereof, wherein the mixture comprises a sufficient amount of polysaccharide and chemotherapeutic agent in a ratio suitable for reducing the toxic side-effects in a subject while being effective against the particular pathology being addressed, wherein the polysaccharide is selected from group consisting of galactomannans from different plant sources. Arabinogalactan (from *Larix occidentalis*), Rhamnogalacturonan (from potato), Carrageenan (from *Eucheuma* Seaweed), and the Locust Bean Gum (from *Ceratonia siliqua*. The toxic side-effects being defined as those physiological effects (symptoms) realized by the subject resulting from the administration of the chemotherapeutic agent absent the polysaccharide. A sufficient amount of polysaccharide is then understood herein to mean that amount required to minimize or mitigate toxic side-effects resulting from the administration of a pharmaceutical agent.

In another embodiment of the present invention, a pharmaceutical formulation is provided that includes a mixture of one or more polysaccharides and an effective dose of a chemotherapeutic agent in a pharmaceutically acceptable formulation, wherein the polysaccharide is selected from group consisting of galactomannans from plant sources. In one aspect, the mixture in the formulation contains an amount of one or more polysaccharides and a chemotherapeutic agent in a ratio suitable for effectively treating cancer as well as for reducing any toxic side-effect in the subject. In another aspect, the mixture contains an amount of one or more polysaccharides and a chemotherapeutic agent in a ratio suitable for enhancing efficacy of chemotherapeutic effect for treating the cancer. In still a further aspect of the invention, a method is provided for treating cancer in a subject in need thereof that includes administrating an a mixture of one or more polysaccharides and an effective dose of a chemotherapeutic agent formulated so that the chemotherapeutic agent has enhanced therapeutic efficacy and reduced toxic effect upon the subject.

Any of the identified compounds of the present invention can be administered to a subject, including a human, by itself, or in pharmaceutical compositions where it is mixed with suitable carriers or excipients at doses therapeutically effective to prevent, treat or ameliorate a variety of disorders, including those characterized by that outlined herein. A therapeutically effective dose further refers to that amount of the compound sufficient result in the prevention or amelioration of symptoms associated with such disorders. Techniques for formulation and administration of the compounds of the instant invention may be found in Goodman and Gilman's The Pharmacological Basis of Therapeutics, Pergamon Press, latest edition.

The compounds of the present invention can be targeted to specific sites by direct injection into those sites. Compounds designed for use in the central nervous system should be able to cross the blood-brain barrier or be suitable for administration by localized injection.

Pharmaceutical compositions suitable for use in the present invention include compositions wherein the active ingredients are contained in an effective amount to achieve its intended purpose. More specifically, a therapeutically effective amount means an amount effective to prevent development of or alleviate the existing symptoms and underlying pathology of the subject being treating. Determination of the effective amounts is well within the capability of those skilled in the art.

For any compound used in the methods of the present invention, the therapeutically effective dose can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in humans.

A therapeutically effective dose refers to that amount of the compound that results in the attenuation of symptoms or a prolongation of survival in a subject. Toxicity and therapeutic efficacy of such compounds can be determined by standard pharmaceutical procedures in cell cultures or experimental animals, e.g., for determining the LD50 (the dose lethal to 50% of a given population) and the ED50 (the dose therapeutically effective in 50% of a given population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of a patient's condition. Dosage amount and interval can be adjusted individually to provide plasma levels of the active moiety which are sufficient to maintain the desired effects.

In case of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The pharmaceutical compositions of the present invention can be manufactured in a manner that is itself known, e.g., by means of conventional mixing, dissolving, granulating, levigating, emulsifying, encapsulating, entrapping or lyophilizing processes.

Pharmaceutical compositions for use in accordance with the present invention thus can be formulated in conventional manner using one or more physiologically acceptable carriers comprising excipients and auxiliaries that facilitate processing of the active compounds into preparations which can be used pharmaceutically. Proper formulation is dependent upon the route of administration chosen.

For injection, the agents of the invention can be formulated in aqueous solutions, preferably in physiologically compatible buffers such as Hank's solution, Ringer's solution, or physiological saline buffer. For transmucosal administration, penetrants appropriate to the barriers to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage for, e.g., in ampoules or in multidose containers, with an added preservatives. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspension. Suitable lipohilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions.

Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations previously described, the compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

A pharmaceutical carrier for the hydrophobic compounds of the invention is a co-solvent system comprising benzyl alcohol, a non-polar surfactant, a water-miscible organic polymer, and an aqueous phase. Naturally, the proportions of a co-solvent system can be varied considerably without destroying its solubility and toxicity characteristics. Furthermore, the identity of the co-solvent components can be varied.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds can be delivered using a sustained-release system, such as semipermeable matrices of solid hydrophobic polymers containing the therapeutic agent. Various of sustained-release materials have been established and are well known to those skilled in the art. Sustained-release capsules can, depending on their chemical nature, release the compounds for a few weeks up to over 100 days. Depending on the chemical nature and the biological stability of the therapeutic reagent, additional strategies for protein stabilization can be employed.

The pharmaceutical compositions also can comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration can, e.g., include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the compound in a local rather than systemic manner, e.g., via injection of the compound directly into an affected area, often in a depot or sustained release formulation.

Furthermore, one can administer the compound in a targeted drug delivery system, e.g., in a liposome coated with an antibody specific for affected cells. The liposomes will be targeted to and taken up selectively by the cells.

The compositions can, if desired, be presented in a pack or dispenser device which can contain one or more unit dosage forms containing the active ingredient. The pack can, e.g., comprise metal or plastic foil, such as a blister pack. The pack or dispenser device can be accompanied by instruction for administration. Compositions comprising a compound of the invention formulated in a compatible pharmaceutical carrier can also be prepared, placed in an appropriate container, and labeled for treatment of an indicated condition. Suitable conditions indicated on the label can include treatment of a disease such as described herein.

Pharmaceutically acceptable carriers are commonly added in typical drug formulations. For example, in oral formulations, hydroxypropyl cellulose, colloidal silicon dioxide, magnesium carbonate, methacrylic acid copolymer, starch, talc, sugar sphere, sucrose, polyethylene glycol, polysorbate 80, and titanium dioxide: croscarmeloose sodium, edible inks, gelatin, lactose monohodrate, magnesium stearate, povidone, sodium layryl sulfate, carnuba bax, crospovidone, hydroxypropyl methylcellulose, lactose, microcrystalline cellulose, and other ingredients may be used. For example, galactomannan has been used as a carrier for oral delivery of agents, which are in a non-liquid form. See U.S. Pat. Nos. 4,447,337; 5,128,143; and 6,063,402, the entire teaching of which is incorporated herein by reference.

EXAMPLES

Example 1

Structure of Galactomannan

The galactomannan oligomer of the present invention is a polysaccharide. In one aspect it has an average molecular weight of about 48,000 D. Shown below is the acceptable chemical nomenclature and structural formula for the galactomann of the present invention. Also shown is the stereochemical configuration.

Full chemical name: (((1,4)-linked β-D-mannopyranose) 17-((1,6)-linked-β-D-galactopyranose)10)12).

A backbone composed of linear (1→4)-β-D-Mannopyranosyl units, to which single β-D-Galactopyranosyl is attached by (1→6) linkage as illustrated below:

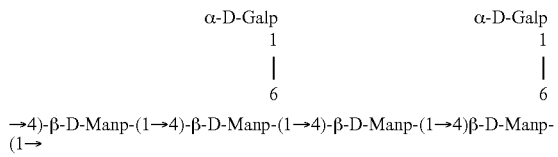

Figure 2:
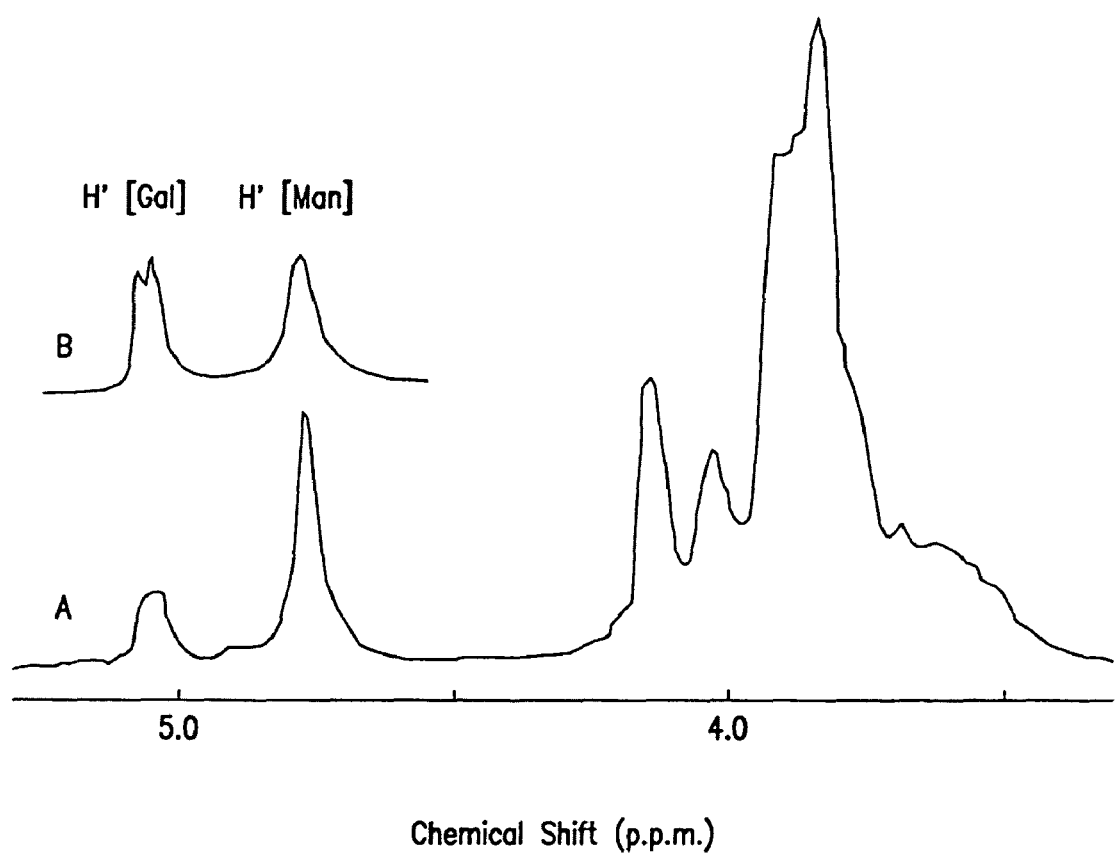
FIG. 2 is a graphical representation of the results of 1H-NMR spectrum of the galactomannan of the invention (from guar gum) and galactomannan from carob (locust bean) gum.

FIG. 2 shows the structure of the galactomannan polysaccharide of the present invention as determined by Nuclear Magnetic Resonance (NMR). The galactomannan of the present invention was compared to galactomannan from Carob (locust bean) gum. An easy identification of the two principal sugar residues, that is mannose (Man) and galactose (Gal), comes from two peaks, at 4.8 p.p.m. (a doublet), respectively, since the ratio of Man/Gal in the galactomannan from guar gum (the galactomannan of the present invention) is 1.7:1 and that in the galactomannan from carob gum (*Ceratonia siliqua*) is 4:1.

Figure 3:
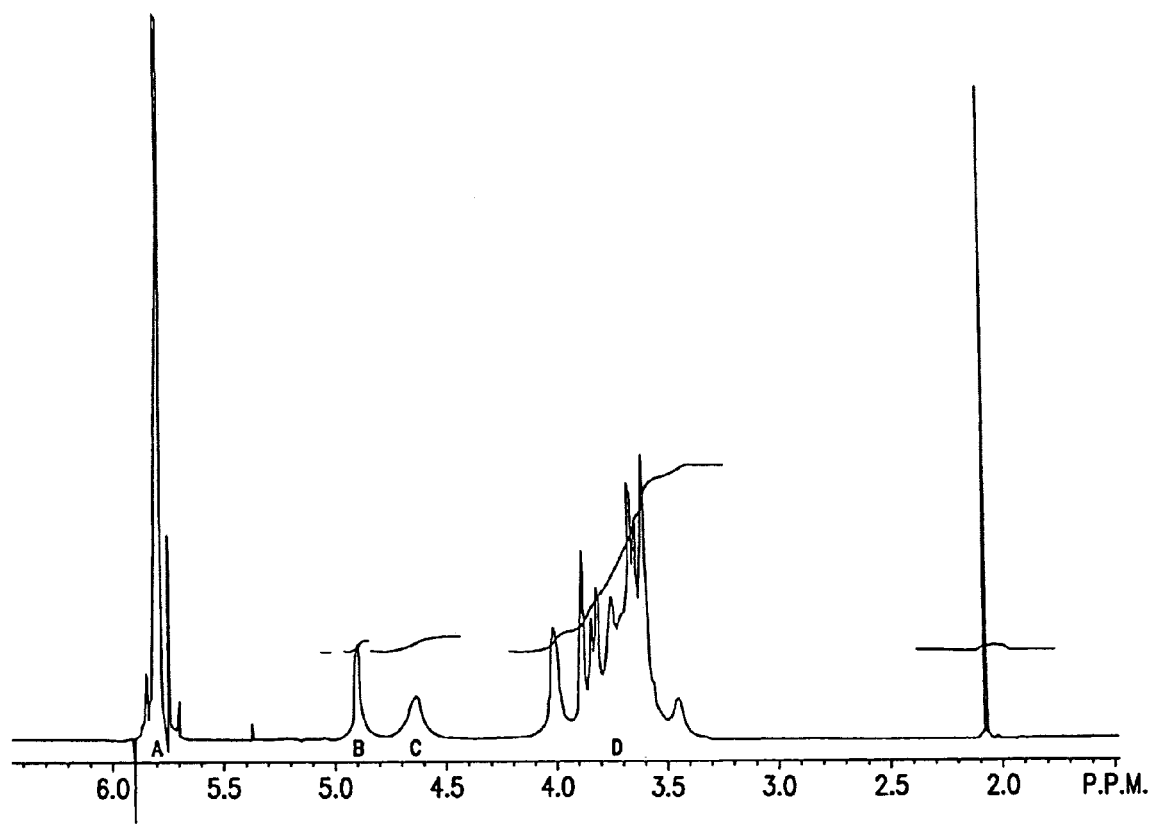
FIG. 3 is the Fourier transform of the 1H-NMR results shown in FIG. 2.

FIG. 3 shows the Fourier Transform 1 H-NMR spectrum of the guar gum galactomannan of the present invention. The signal for the galactose anomeric protons appears at approximately 4.9 ppm (doublet). The signal for the mannose anomeric protons appears at approximately 4.6 ppm (broad signal). These signals are completely completely separated from those of the free monosachharides; the galactose a proton at 5.1 ppm and (3 at 4.5 ppm, the mannose a at 4.8 ppm and (β at 5.0 ppm. The ratio of mannose to galactose units can be easily calculated for this working standard at 1.7.

Figure 4:
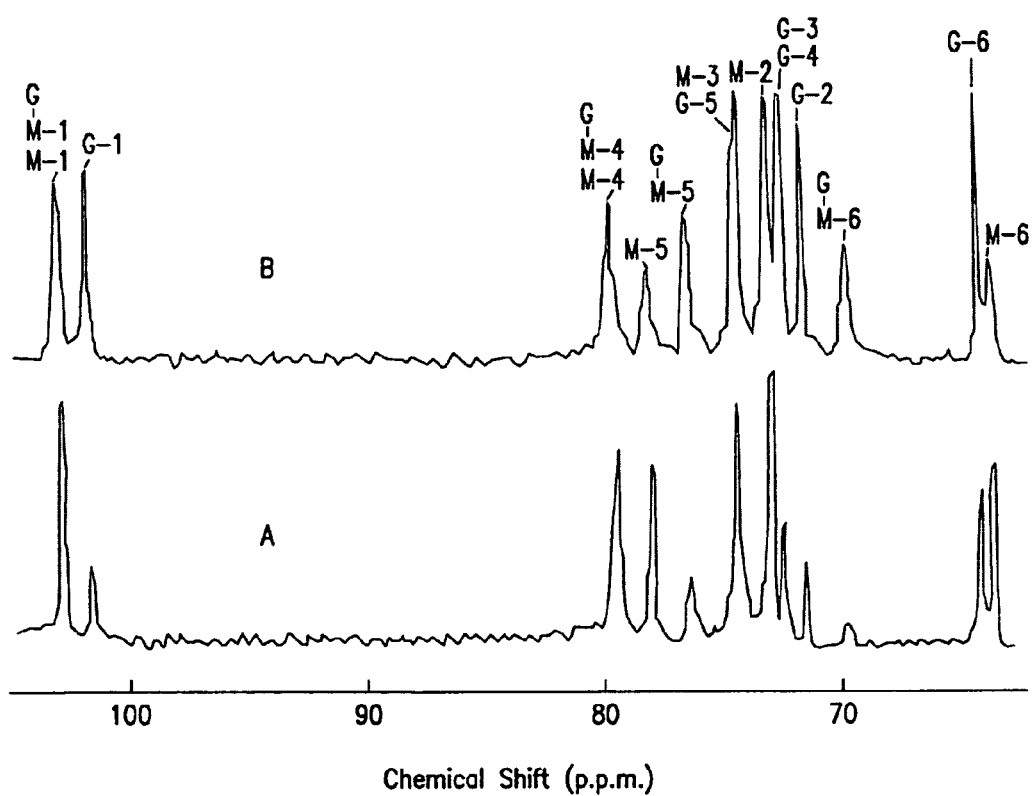
FIG. 4 is a graphical representation of the results of 13C-NMR spectrum of the galactomannan of the invention (from guar gum) and galactomannan from carob gum.

FIG. 4 shows the 13C-NMR spectrum of the galactomannan of the present invention, showing detailed positions of the chemical shifts and their intensities. This study confirms the above chemical structure for the galactomannan.

FIG. 4 illustrate the following:

1) All three sugars are seen in the NMR spectrum, i.e., β-D-galactopyranosyl, 4-0-β-D-mannopyranosyl (unsubstituted) and 4,6-Di-O-β-D-mannopyranosyl (substituted). The positions of signals from C1 to C6 for all the three sugars, that is G-1 to G-6, M-1 to M-6, and GM-1 to GM-6, respectively, are shown in the FIG. (the positions of G-2 and G4, M-1 and GM-1, M-2 and GM-2, M-3 and GM-3, M-4 and GM-4 are coincident within these pairs).

2) The positions of signals for galactose in the NMR spectrum completely correspond to those of carbon atoms of free galactopyranose, providing evidence for the absence of substituents at positions of Gal units in the galactomannan.

3) Substitution of certain mannose residues is at C-6 (because the shift of the signal from 63.6 p.p.m. for "normal" unsubstituted methylene carbon to "substituted" one at 69.6 p.p.m., along with a shift of the adjacent C-5 signal from a "normal" 78 p.p.m. to 76.4 p.p.m.); the 63.6 p.p.m. Shift for the methylene carbons are well documented.

4) C-1 of galactose residue is involved in formation of galactoside bond (because compared to C-1 of free galactose that one in the NMR spectrum had a lowfield shift +6.5 p.p.m.).

5) Mannose residues are attached to each other "head-to-tail", forming a (1→4) backbone chain.

6) There are unsubstituted Man-Man pairs along with substituted, Man (Gal)-Man, Man-Man (Gal), and Man (Gal)-Man (Gal); the NMR spectra of galactomannans from guar gum, carob gum, and clover seeds in the region of C-4 (Man) resonance (split into three peaks) show, that the highest peak at high field (corresponding to unsubstituted Man-Man pairs) is observed for a galactomannan from carob gum (Man/Gal=3.8); the lowest peak corresponds to a galactomannan from clover seeds (Man/Gal=1.4), and the intermediate peak corresponds to the galactomannan of the invention (a galactomannan from guar gum, Man/Gal=1.7).

7) The ratio of mannose to galactose in the galactomannan of the invention (the galactomannan from guar gum) was 1.7 (that was the integral intensity ratio of C-1 signal of mannose and galactose, and also calculated from dual frequencies for unsubstituted and substituted Man residues, measured from C-4 (Man) resonance.

8) The relative frequency of unsubstituted Man-Man pairs was 22%, that of Man (Gal)-Man and Man-Man (Gal) total was 48%, and of totally substituted pairs Man (Gal)-Man (Gal) was 30% (from intensities of the split C-4 signals into respective three lines/peaks).

Figure 5:
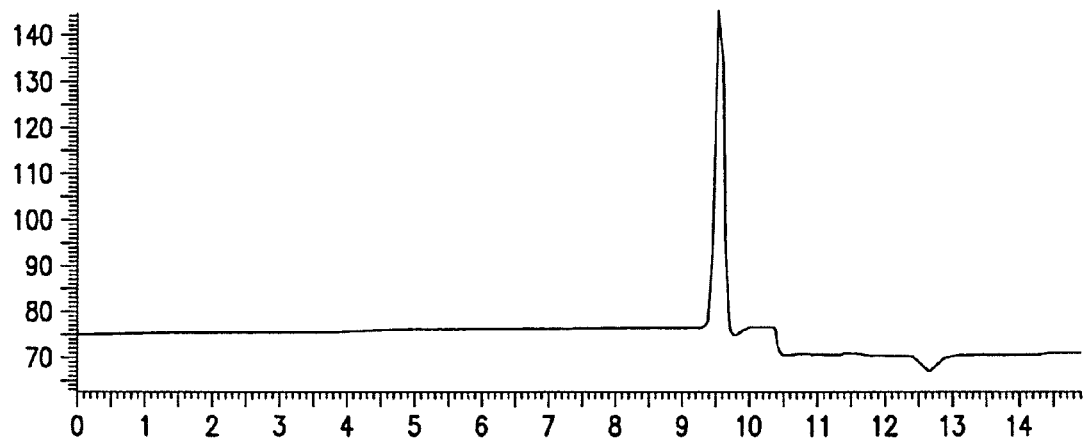
FIG. 5 is a graphical representation of the results of HPLC/RI-MALLS profile of the galactomannan of the present invention.
Figure 5:
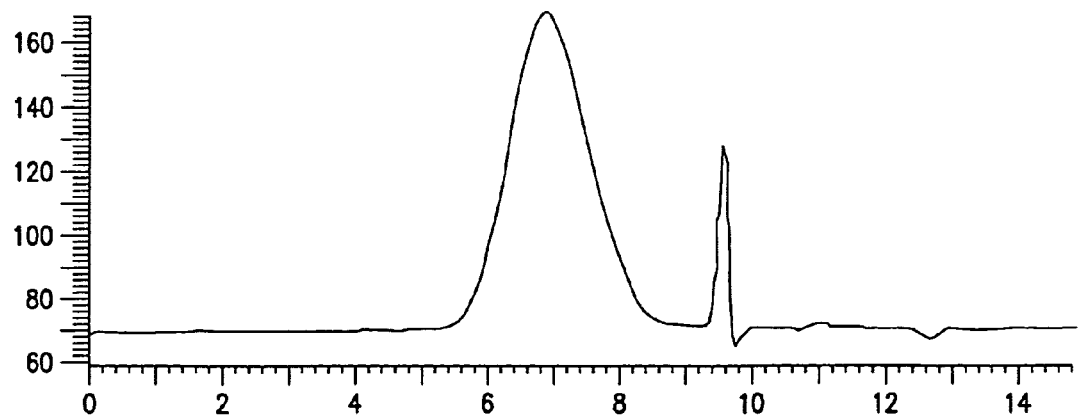
Figure 6A:
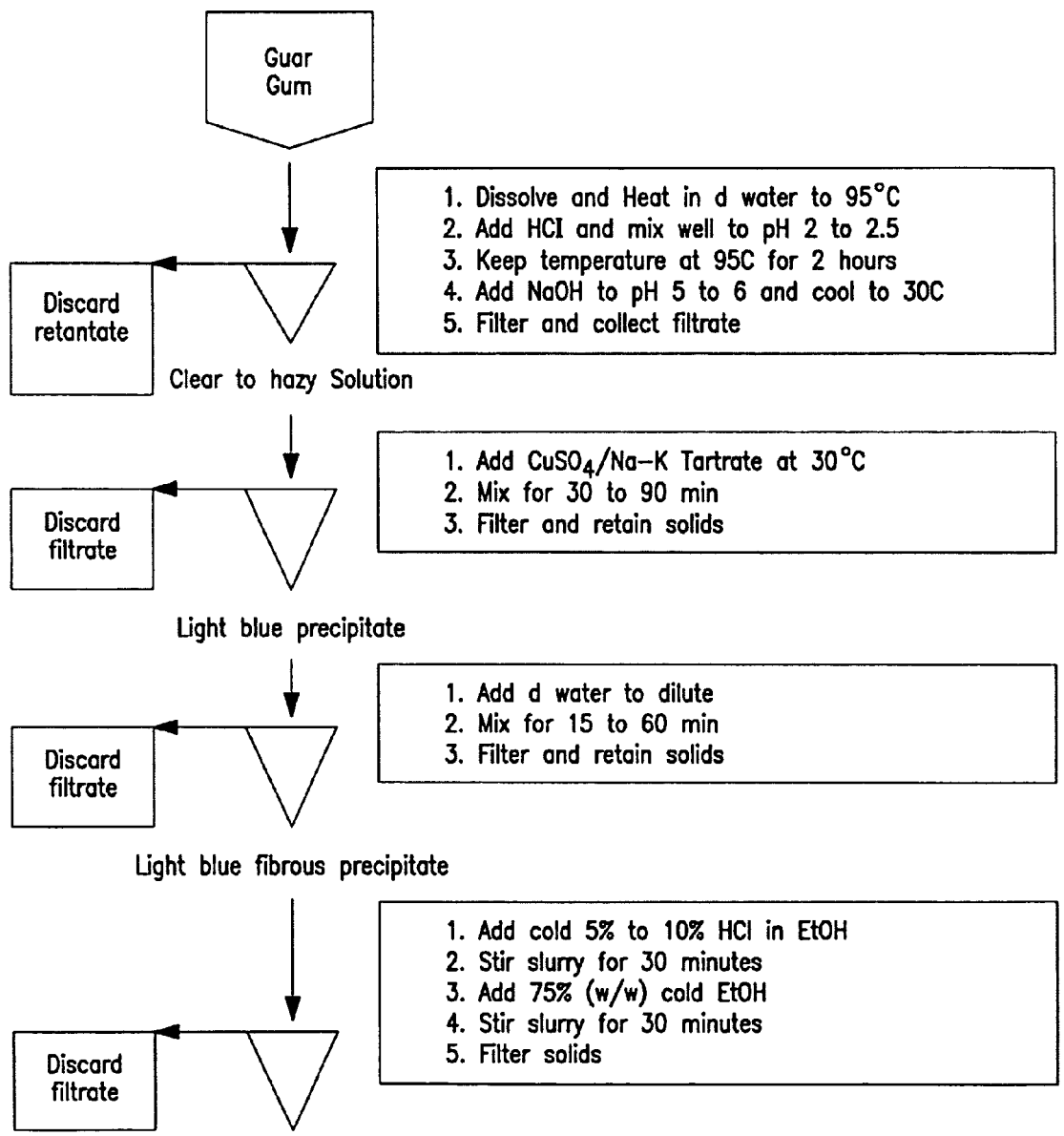
FIG. 6 is a schematic representation of the manufacturing and purification process to produce the galactomannan of the present invention.
Figure 6B:
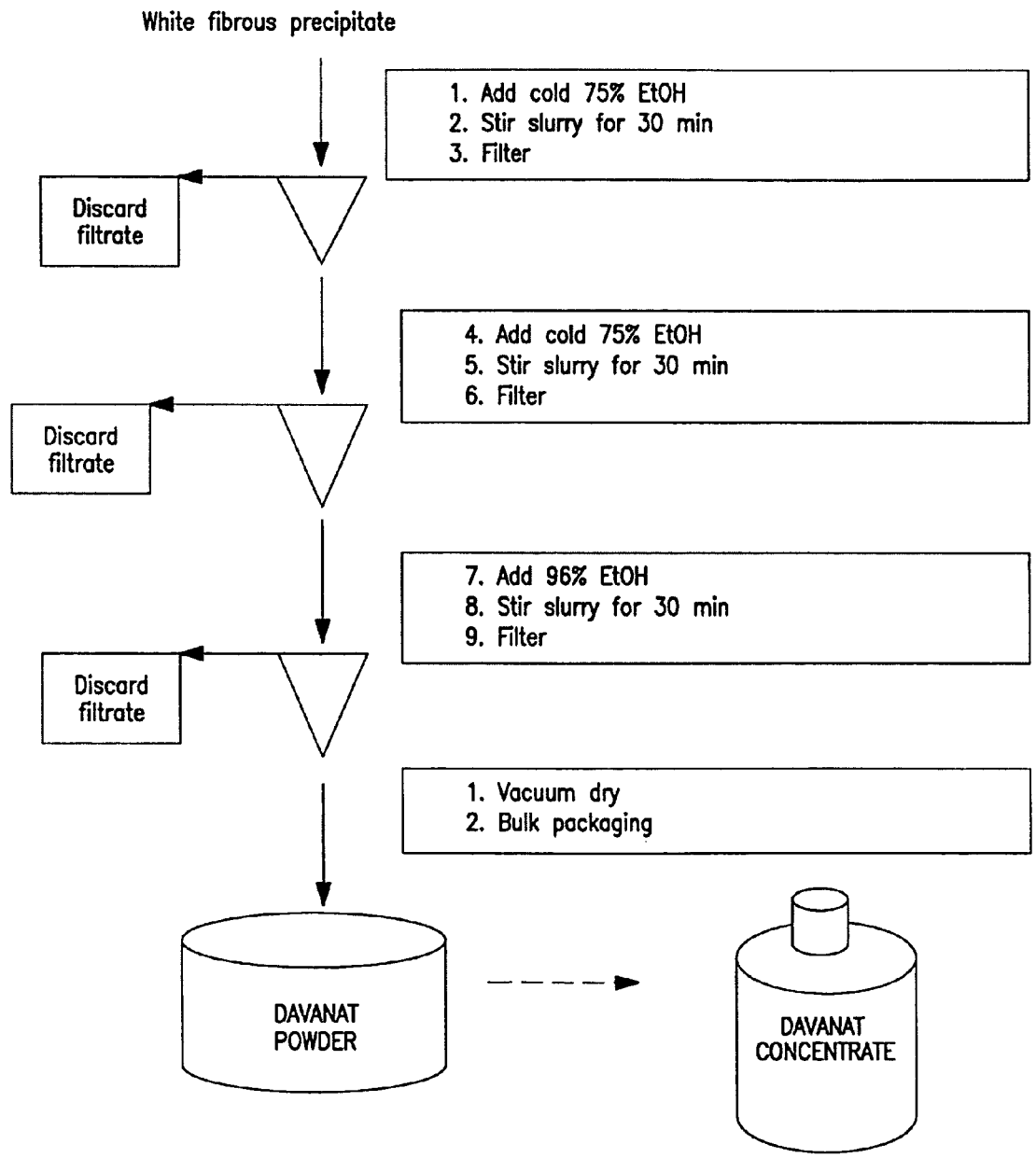

FIG. 5 shows the quantitation and molecular weight of the galactomannan of the present invention by HPLC/RI-MALLS (high performance liquid chromatography/refractive index-multi-angle laser light scattering).

High Performance Liquid Chromatography (HPLC) using Gel Permeation Chromatography (GPC) separation technology (also known as Size Exclusion Chromatograpy—SEC) is a well-established technique for the characterization of polymers. GPC in combination with Multi-Angle Laser Light Scattering (MALLS) and Refractive Index (RI) detection is a powerful tool for the determination of absolute molecular weights of polymeric carbohydrates. The application of light scattering detection eliminates the necessity for time-consuming conformation-dependent calibrations of the GPC system. Another advantage of GPC-MALLS over classical GPC is that besides molecular weights, additional information concerning radii and conformation in solution can be followed.

The principle of the GPC-MALLS method is based on the fact that light is more strongly scattered by large molecules than by small molecules. During the chromatographic run, the MALLS detector measures the degree of light scattering of a laser beam with detectors placed at fifteen different angles. The output of the light scattering detector is proportional to the multiplication of the concentration and the molecular weight of macromolecules. Therefore, the shape of the light scattering peak is asymmetric. Further, it does not coincide with the RI peak, because the RI detector signal is proportional to the concentration only (see FIG. 5). At any elution time the molecular weight of the polymer eluting from the column can be calculated from the quotient of MALLS and RI signals. A graph of the molecular weight versus the elution volume is obtained and (average) molecular weights and molecular weight distributions can be calculated.

The present investigators have adapted the GPC/IR-MALLS technique to quantitate the drug substance and characterize the molecular weight average and distribution throughout the R&D and scale up phases for the invention. The use of the MALLS analysis removes many factors interfering with MW estimation by the "Classical GPC". GPC separations are based on differences in hydrodynamic volume instead of differences in molecular weight. Differences in molecular conformation, e.g. branching in dextrans, can strongly influence the hydrodynamic volume. Secondly, GPC elution of positively or negatively charged polymers can be non-ideal because of repulsion or attraction by the stationary phase. The GPC-MALLS results are not affected by these chromatographical drawbacks, and absolute molecular weights are obtained.

The use of dual monitoring of the HPLC elution profile of the galactomannan of the invention provides two important chemical specifications, e.g., quantitative measurement by the Refractive Index signal and the absolute molecular weight by the Multi Angle Laser Light Scattering (MALLS) detector. Furthermore, these chromatograms can provide data on molecular stability and breakdown derivatives of the galactomannan of the invention.

Example 2

Purification and Manufacturing Process

Shown in FIG. 5 is a flow chart of an example for a purification and manufacturing process for a galactomannan of the present invention. High grade Guar gum is dissolved in warm water at 1% at 45° C. for 2 hr. The pH is reduced to 2.2 with 1 M HCl and solution is heated to 95° C. for 2 hours. Then pH is adjust to 5.8 with 1 M NaOH. The solution is then cool to 20° C. and filter with glass filter. Next CuSO4/Na—K tartrate is added and the precipitate is collected on 200 mesh filter, wash with water solution and than washed in 5% HCl in 960% EtOH. Then washed with 75% EtOH and twice with 96% EtOH. And finally vacuum freeze-dried as white solids. Galactomannan, from a readily available source (e.g., Guar gum), was selected for process optimization and manufacturing. The soluble galactomannan oligomer was tested in-vivo (in animals) for both efficacy and overall reduction of toxicity.

The manufacturing process described above produces a product in the form of a highly soluble oligomer of Galactomannan (GM) from certified premium Guar Gum powder (from seeds of *Cyamopsis tetragonoloba*). The process is designed to generate a highly pure soluble and homogeneous oligomer with an average molecular weight in the range of about 48,000 daltons, and mannose to galactose ratio in the range of about 1:7. The process incorporates four major phases; controlled depolymerization to produce the desired galactomannan oligomer and three purification steps, removal of insoluble impurities, removal of water soluble impurities, removal of organic soluble impurities, and finally freeze drying to generate a pure and stable form of galactomannan powder.

Galactomannan can be packaged and delivered as a sterile concentrated solution in a single use vial, while bulk galactomannan can be produced and stored as powder. The process described herein is for both bulk drug and final drug product. The galactomannan drug product can be combined and administered together with a pharmaceutical like 5-fluorouracil to form the active ingredients of a pharmaceutical preparation. The drug product contains normal saline for infusion (about 0.9 M sodium chloride in water) and has a pH of about 6.5.

Examples 3-5

Efficacy Studies

The galactomannan of the present invention is a galactomannan derivative comprising exposed galactose moieties attached to a mannose backbone. The compound is thought to interact with galactose-binding lectins or galectins that are generally located on cell surfaces. Lectins are carbohydrate-binding proteins, typically located on the cell surface, which mediate various types of cellular interactions. It is generally accepted that lectins mediate many biological recognition events in plants and in animal tissues, and in tumor cell lines. Lectins play a role in cell-cell adhesion, and in the organization of the extracellular matrix. At the cell surface, lectins can act as receptors involved in selective intercellular adhesion and cell migration, recognition of circulating glycoproteins, and modulation of cell-cell and cell-matrix interactions. Galectins are members of a family of β-galactoside-binding lectins with related amino acid sequences. Galectins and lectins have been the target of many experimental agents (monoclonal antibodies, simple sugars, and some polysaccharides, such as pectins) which allegedly interact with them on the cancer cell surface. The use of some of these agents has been shown to result in inhibition of tumor cell colony development.

Because of its rather simple and relatively regular structure, the galactomannan of the invention can be distinctly identified and characterized, unlike many known polysaccharides. Its exposed galactose residues can readily interact with biological targets, such as lectins and galectins, thereby modulating signal transduction, cell-cell interactions or other functions. It thus can block the actions of galectins (or other receptors), thereby competing with their specific (or non-specific) ligands. When combined and administered with 5-FU, the galactomannan of the invention enhances the antineoplastic effects of 5-FU in animal models of colorectal cancer, although the precise mechanism has yet to be defined.

For over 40 years, 5-fluorouracil (5-FU) has been the standard first-line agent used either alone, or in combination with, other agents in the treatment of metastatic colorectal cancer. Preliminary animal studies with a variety of soluble galactomannan oligomers have shown promising response to the combination therapy of 5-FU and galactomannan with mannose to galactose ratio of 1:7.

Three non-clinical pharmacology studies were conducted to assess the effects of the galactomannan of the invention alone or in combination with 5-FU in tumor-bearing mice. Results from two separate experiments in athymic MCr-nu mice implanted with human colon tumor COLO 205 indicated that the galactomannan of the invention enhanced the antineoplastic action of 5-FU.

Example 3

Figure 7:
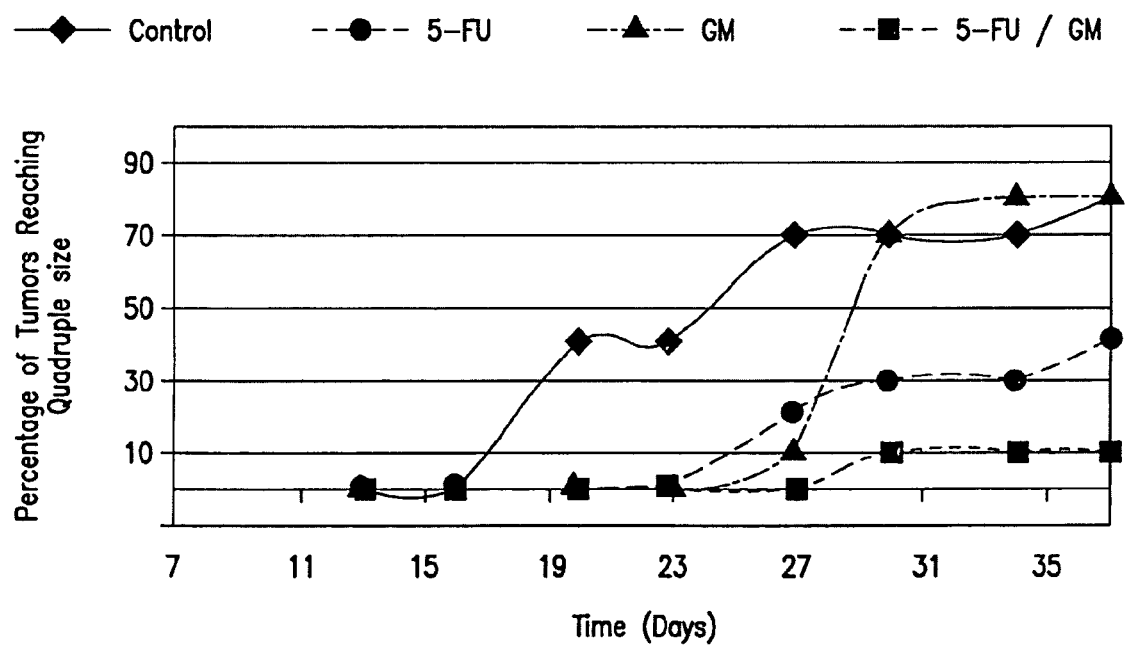
FIG. 7 is a graph summary of the results of the first part of the efficacy study described in Example 3.
Figure 8:
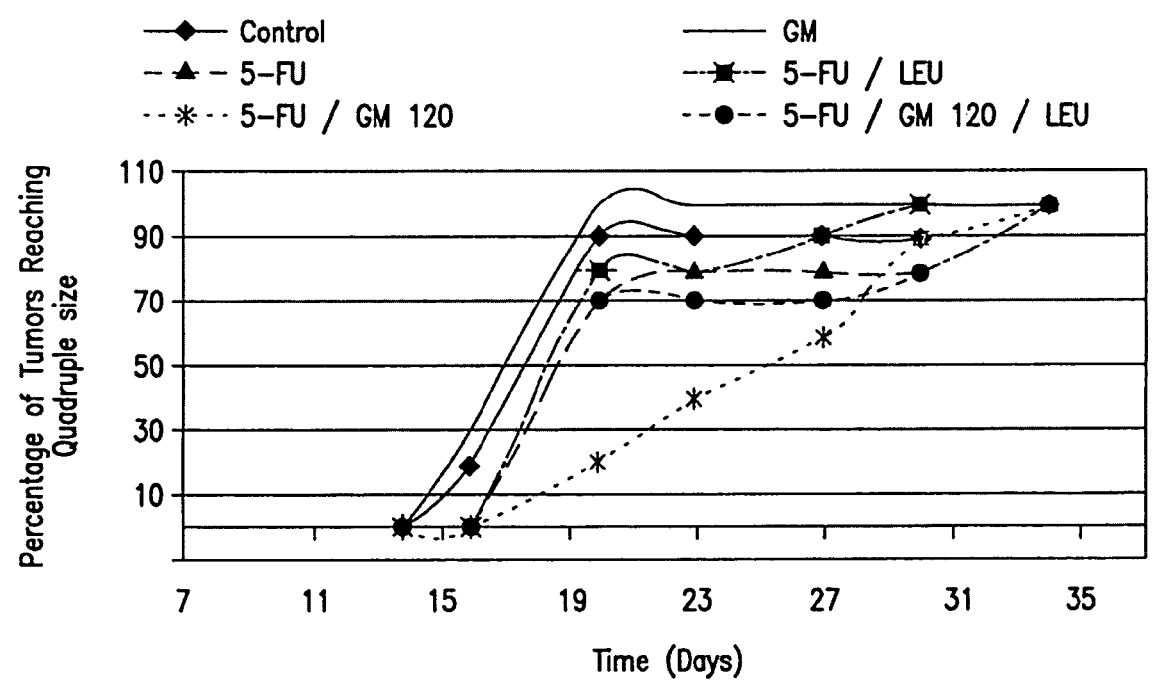
FIG. 8 is a graph summary of the results of the second part of the efficacy study described in Example 3.
Figure 9:
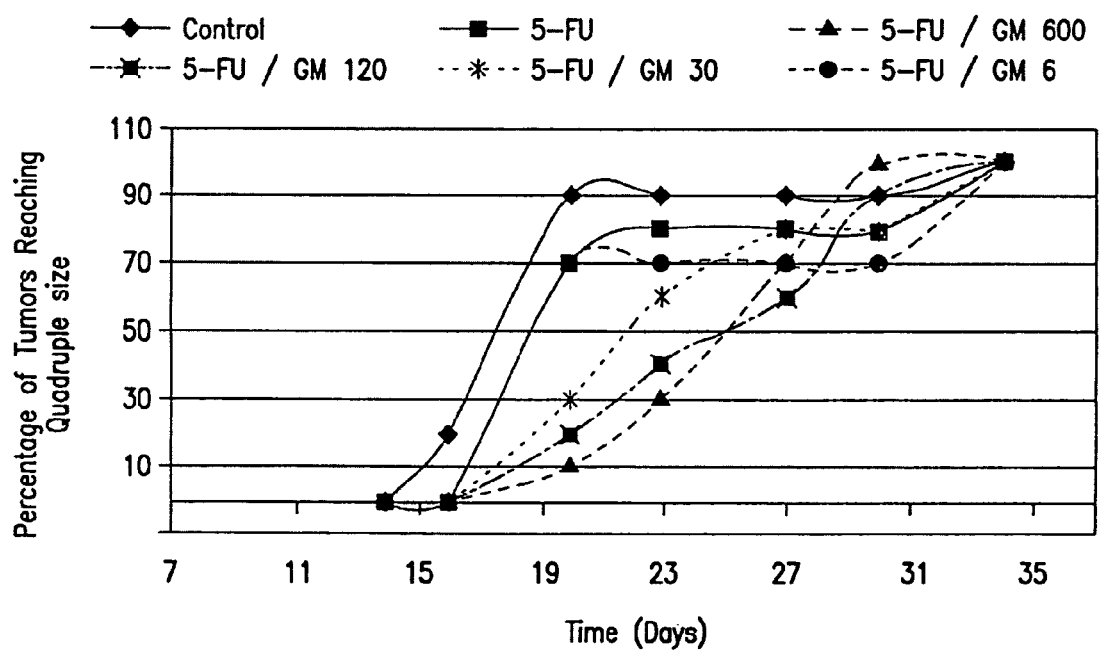
FIG. 9 is a graph summary of the results of the efficacy study described in Example 4.

Greater Decrease in Tumor Growth when Anti-Tumor Drug 5-FU Administered in the Presence of Galactomannan In this study, using human colon tumor COLO 205 in athymic MCr-nu mice indicated that intravenous injections of 5-FU significantly decreased tumor growth. The results of this study are summarized in FIG. 7. However, when the galactomannan of the invention at 120 mg/kg/day (360 mg/m2) combined with the above dose of 5-FU was administered, the tumor growth was further decreased for both mean tumor size and growth rate. The time required to quadruple tumor weight increased from 23.5 days for 5-FU alone to 56.0 days for the galactomannan of the invention/5-FU combination versus 12.5 days for the control (untreated) animals. The results of this study are summarized in FIG. 8. The both studies were conducted as follows.

The galactomannan from *Cyamopsis tetragonoloba* was administered intravenously (i.v.) once every four days for a total of three injections (q4d×3) at a doses of 120 mg/kg/dose (360 mg/m2/dose), or was co-administered as one injection with 5-FU on the same q4d×3 treatment schedule at doses of 120 mg/kg/dose of GM and 75 mg/kg/dose (225 mg/m2/dose) of 5-FU. 5-FU alone was administered i.v. on the same q4d×3 treatment schedule at doses of 75 mg/kg/dose (225 mg/m2/dose). 5-FU was formulated in saline fresh on each day of treatment at a concentration of 3.75 mg/mL, at pH 9.2. In the groups where GM and 5-FU were co-administered, GM powder was dissolved in the 5-FU solution to yield the GM concentration of 6 mg/mL and 5-FU concentration of 3.75 mg/mL. Both individual compounds and their mixture were administered according to exact body weight with injection volume being 0.2 mL/10 g body weight.

There were a total of four groups of 10 animals each, s.c.-implanted with COLO 205 human colon tumor xenografts. The groups were treated on day 13 after tumor implantation on q4d×3 schedule as follows: 1) saline (NaCl, 0.9%), 2) 5-FU (75 mg/kg/dose), 3) GM (120 mg/kg/dose), 4) 5-FU (75 mg/kg/dose)+GM (120 mg/kg/dose).

Control untreated tumors grew well in all mice, with a median to quadrupling of tumor volume equal to 12.5 days. There was no tumor regression after 56 days of the study, and there was practically no tumor reduction. Median tumor volume increased from 111 mm3 at treatment initiation (in this case with saline only) to 2058 mm3 after 5-8 weeks. Mean survival time was equal to 14.2 days.

A dosage of 75 mg/kg/dose of 5-FU (i.e., 225 mg/kg total dose over 8 days) was in excess of the maximum tolerated dosage and produced treatment-related deaths for three of ten mice within two weeks. The treatment caused a delay in a median to quadrupling of tumor volume from 12.5 to 23.7 days. Again, there was no tumor regression after 56 days of the study; however, two relatively small tumors were observed that grew from 75 mm3 each at initiation of treatment to 126 mm3 and 567 mm3 by the end of the study. Median tumor volume increased from 101 mm3 at treatment initiation to 2254 mm3 after 56 days of the study. Mean survival time shifted from 14.2 days (control, untreated animals) to 23.7 days.

GM, at a dosage of 120 mg/kg/dose administered alone on a q4d×3 schedule, was well tolerated. No deaths or body weight loss was observed. The median to quadrupling of tumor volume equaled 15.5 days, that is slightly longer than the value for untreated animals (12:5 days). There was no tumor regression after 56 days of study, however, two relatively small tumors (compared to median tumor volume) were observed that grew from 100 mm3 and 126 mm3, at initiation of treatment, to 270 mm3 and 729 m3, respectively, by the end of the study. Median tumor volume increased from 100 mm3 at treatment initiation to 1813 mm3 after 56 days of the study, that is noticeably less compared to 2058 mm3 for untreated animals, and 2254 mm3 for 5-FU (75 mg/kg/dose)-treated animals. Mean survival time was prolonged from 14.2 days (control, untreated animals) to 19.2 days.

Co-administration of GM (120 mg/kg/dose) and 5-FU (75 mg/kg/dose) on a q4d×3 schedule brought a remarkable effect. It caused a significant delay in quadrupling of tumor volume, from 12.5 days for untreated animals (control) and 23.7 and 15.5 days for 5-FU alone and GM alone, respectively, to 56.0 days for their combination. There was one tumor that completely disappeared by the end of the study. This tumor went from the initial 75 mm3 to 126 mm3 on the third day after the first injection to 144 mm3 after the second and third injections, and, after two weeks on the study, decreased to barely detectable, and then completely disappeared. Two more tumors were relatively small in size, that is less than 20% of that of control value, by the end of the study. Overall, median tumor volume increased from 111 mm3 at treatment initiation to only 379 mm3 after 56 days of study, a value significantly less than that for untreated animals or animals treated with 5-FU alone. Mean survival time increased from 14.2 days (control, untreated animals) and 23.7 days (5-FU treatment) to 44.2 days for the combination treatment.

Example 4

Compatibility of Galactomannan/5-FU with Leucovorin

A second study using COLO 205 tumors in mice evaluated the compatibility of the investigator's galactomannan/5-FU with Leucovorin (given orally, 25 mg/kg/dose) and dose escalation of galactomanna from 6 to 600 mg/kg/day (or 18 to 1800 mg/m2). The combination of 5-FU+galactomannan (at 48 mg/kg and 120 mg/kg, respectively) had the best antitumor response for both mean tumor size and time required to quadruple tumor weight, being superior to the 5-FU alone or 5-FU+Leucovorin combination.

The principal differences with the study described in Example 3 were that (a) the galactomannan was from another source, of a different size (molecular weight) and with a different Man/Gal ratio, (b) there were four consecutive injections, not three, (c) there were four doses of the galactomannan tested, not one, (d) 5-FU was administered (i.v.) in 48 mg/kg/dose, not 75 mg/kg/dose, as in the first study, and (e) galactomannan (i.v. injection) was compared with leucovorin (oral gavage, administered two hours after 5-FU) in terms of efficacy and toxicity. The galactomannan from *C. tetragonoloba* was administered intravenously (i.v.) once every four days for a total of four injections (q4d×4) at a dosage of 120 mg/kg/dose (360 mg/m2/dose) or was co-administered as one injection with 5-FU on the same q4d×4 treatment schedule at a dosage of 6, 30, 120, and 600 mg/kg/dose (18, 90, 360, and 1800 mg/m2/dose, respectively) of GM and 48 mg/kg/dose (144 mg/m2/dose) dose of 5-FU. 5-FU alone was administered i.v. on the same q4d×4 treatment schedule at dosages of 48 mg/kg/dose. 5-FU was formulated in saline fresh on each day of treatment at a concentration of 4.8 mg/mL, at pH 9.2. In the groups where GM and 5-FU were co-administered, GM powder was dissolved in the 5-FU solution to yield the GM concentration of 0.6, 3.0, 12, and 60 mg/mL and 5-FU concentration of 4.8 mg/mL. Leucovorin powder (clinical formulation, Leucovorin calcium for injection) was reconstituted with water for injection to yield a concentration of 10 mg/mL. On each day of treatment the stock solution was diluted with water for injection to yield a concentration of 2.5 mg/mL. 5-FU and GM and their mixture with each other and leucovorin were administered by exact body weight with injection or p.o. volume being 0.1 mL/10 g body weight.

Two more combination-treatment groups were also included in the study. One group of mice was treated with 5-FU (48 mg/kg/dose, i.v., q4d×4), followed by oral gavage (p.o.) with leucovorin, administered two hours after 5-FU at a dosage of 25 mg/kg/dose. Another two groups of mice were treated with 5-FU in a combination with the galactomannan (48 mg/kg/dose and 120 mg/kg/dose, respectively, i.v., q4d×4), followed by p.o. leucovorin treatment, administered at a dosage of 25 mg/kg/dose two hours after 5-FU plus the galactomannan.

There were a total of nine groups of 10 animals each, s.c.-implanted with COLO 205 human colon tumor xenografts. The groups were treated on day 14 after tumor implantation on q4d×4 schedule as follows: 1) Saline (NaCl, 0.9%), 2) 5-FU (48 mg/kg/dose), 3) GM (120 mg/kg/dose), 4) 5-FU (48 mg/kg/dose)+GM (6 mg/kg/dose), 5) 5-FU (48 mg/kg/dose)+GM (30 mg/kg/dose), (6) 5-FU (48 mg/kg/dose)+GM (120 mg/kg/dose), (7) 5-FU (48 mg/kg/dose)+GM (600 mg/kg/dose), (8) 5-FU (48 mg/kg/dose)+leucovorin (oral, 25 mg/kg/dose), and (9) 5-FU (48 mg/kg/dose)+leucovorin (oral, 25 mg/kg/dose)+GM (120 mg/kg/dose). The last two groups were introduced to compare the effect of leucovorin with that of the galactomannan.

No mice died in this study. As in the study, described in Example 3, control untreated tumors grew well in all mice. The median to quadrupling of tumor volume equaled 7.2 days. No tumor regression or reduction occurred after 13 days of the study. Median tumor volume increased from 162 mm3 at treatment initiation (in this case with saline only) to 1288 mm3 after 13 days.

A dosage of 48 mg/kg/dose of 5-FU (that is, 192 mg/kg total dose over 12 days) was well tolerated and produced some growth delay in the median to quadrupling of tumor volume, increasing it from 7.2 to 8.7 days. Two tumors in the group of 10 mice were significantly (three times or more) smaller, compared with the median tumor size, after 13 days of treatment, growing from 100 and 163 mm3 at initiation of treatment to 270 mm3 and 138 mm3, respectively, by the end of the study. Median tumor volume increased from 172 mm3 at treatment initiation to 800 mm3 after 13 days of the study, less than the control value 1288 mm3.

GM at a dosage of 120 mg/kg/dose administered alone on a q4d×4 schedule did not delay growth (the median to quadrupling of tumor volume equaled 6.9 days, compared to that of 7.2 days in the control group). No tumor regression occurred after 13 days of study, and no relatively small tumors (compared to median tumor volume) were observed. Median tumor volume increased from 157 mm3 at treatment initiation to 1152 mm3, a value essentially equal to that of the untreated animals (1288 mm3).

Co-administration of 5-FU (48 mg/kg/dose) and GM (6, 30, 120, and 600 mg/kg/dose) on a q4d×4 schedule was well tolerated at all dosages tested. It caused a significant delay in quadrupling of tumor volume, from 7.2 days for untreated animals (control) and 8.7 and 6.9 days for 5-FU alone and GM alone, to 14.8, 13.5, 16.5, and 16.2 days, respectively. The best results were obtained with a combination of 5-FU and the 120 mg/kg/dose galactomannan, which resulted in a median tumor volume of 540 mm3 at day 13, the day after the final day of treatment, compared with that of 800 mm3 for 5-FU treatment alone. Also, median days to quadrupling of tumor volume was almost twice as much for the 5-FU+GM 120 mg/kg/dose than for the 5-FU alone.

Treatment with 5-FU in the presence of leucovorin did not add anything to the efficacy of the drug. Median days to quadrupling of tumor weight even decreased from 8.7 days to 8.2 days, and tumor weight at Day 13 from treatment initiation slightly decreased as median (from 800 mg to 775 mg), but noticeably increased as mean (from 734 mg to 969 mg). Addition of the galactomannan 120 mg/kg/dose to the combination of 5-FU and leucovorin only slightly improved the situation, by increasing median days to quadrupling of tumor weight back to 8.7 days, and slightly decreasing tumor weight at Day 13 from 800 mg (5-FU) and 775 mg (5-FU/leucovorin) to 725 mg as median, and from 734 mg and 969 mg, respectively, to 706 mg as mean.

Example 5

Figure 10:
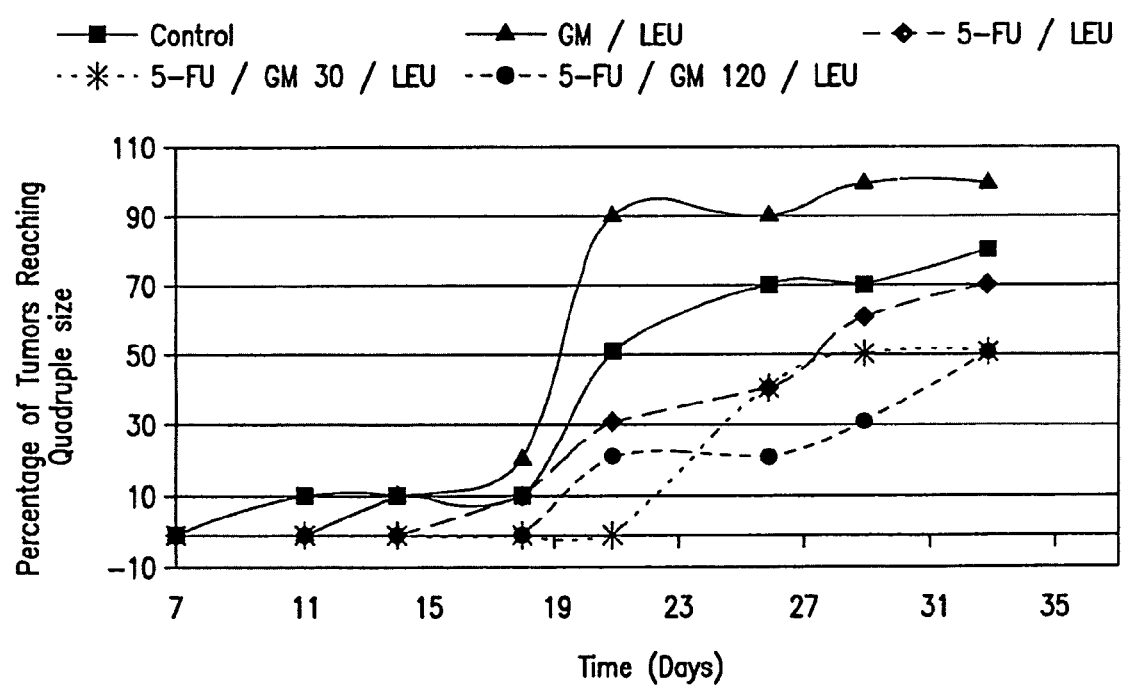
FIG. 10 is a graph summary of the results of the efficacy study described in Example 5.

Anti-Tumor Efficacy of Combinations of 5-FU and Galactomannan at Different Dosages A second human colon tumor, HT-29, in NU/NU-nuBR nude mice was studied to evaluate the anti-tumor efficacy of the combinations of 5-FU at 48 mg/kg/dose, galactomannan at 30 and 120 mg/kg/dose given I.V. every 4 days for a total of four injections. All groups received oral leucovorin, 25 mg/kg/dose. At Day 33, the mean tumor volume was lowest for 5-FU+leucovorin+galactomannan 120 mg/kg. These findings demonstrated that the galactomannan enhanced the anti-tumor activity of 5-FU in the presence of leucovorin. The results of this study are summarized in FIG. 10.

Figure 11:
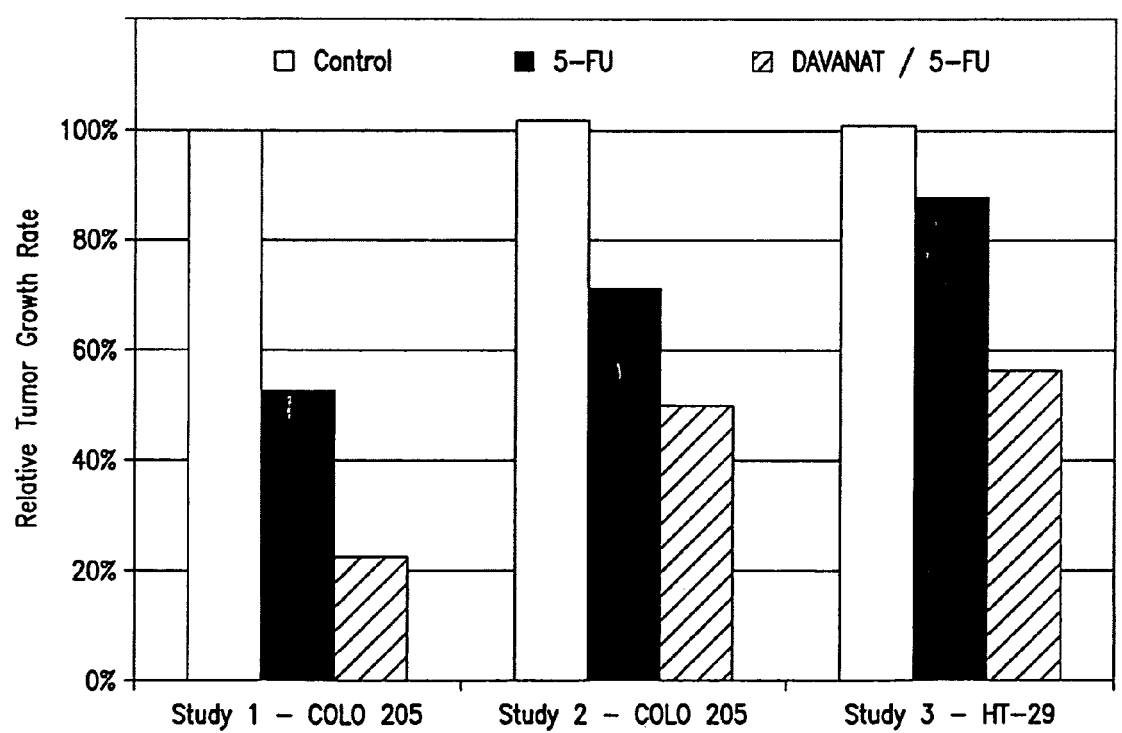
FIG. 11 is a graph summary of the results of the three efficacy studies described in Examples 3, 4, and 5.

The results of all three efficacy studies are summarized together in FIG. 11 for comparison.

The principal differences from the second study were that (a) another tumor (HT-29) was used, and (b) leucovorin was added to the treatment regimen. The GM was co-administered i.v. via tail vein injection once every four days for a total of four injections (q4d×4) at a doses of 30 and 120 mg/kg/dose as one injection with 5-FU (48 mg/kg/dose), followed by oral gavage (p.o.) of leucovorin, administered two hours after the injection, at a dose of 25 mg/kg/dose on the same q4d×4 schedule. GM or 5-FU were administered also on the same q4d×4 treatment schedule at doses of 120 mg/kg/dose (GM) or 48 mg/kg/dose (5-FU), followed by 25 mg/kg of leucovorin, administered two hours later.

GM was formulated in 0.9% sterile saline fresh on each day of treatment at a concentration of 12 mg/mL. Leucovorin powder (clinical formulation, Leucovorin calcium for injection) was reconstituted with 0.9% sterile saline to yield a concentration of 2.5 mg/mL. 5-FU was formulated in 0.9% sterile saline fresh on each day of treatment at a concentration of 4.80 mg/mL, at pH 9.2. In the groups where GM and 5-FU were co-administered, GM powder and 5-FU were dissolved in 0.9% fresh saline to yield the GM concentration of 3.0 mg/mL or 12 mg/mL, and 5-FU concentration of 4.80 mg/mL. Both individual compounds and their mixture were administered according to exact body weight with injection volume being 0.1 mL/10 g body weight.

There were a total of five groups of 10 animals each, s.c.-implanted with HT-29 human colon carcinoma xenografts. The groups were treated on day 7 after tumor implantation on q4d×4 schedule as follows: 1) Saline (NaCl, 0.9%), 2) GM (120 mg/kg/dose)+leucovorin (p.o., 25 mg/kg/dose), 3) 5-FU (48 mg/kg/dose)+leucovorin (p.o., 25 mg/kg/dose), 4) 5-FU (48 mg/kg/dose)+GM (30 mg/kg/dose)+leucovorin (p.o., 25 mg/kg/dose), and 5) 5-FU (48 mg/kg/dose)+GM (120 mg/kg/dose)+leucovorin (p.o., 25 mg/kg/dose).

As in the two preceding studies, control (untreated) tumors grew well in all mice, with a median of 13.3 days for quadrupling of tumor volume. Median tumor volume increased from 196 mm3 at treatment initiation (day 7 after tumor implantation) to 1318 mm3 after 26 days.

A dosage of 48 mg/kg/dose of 5-FU (192 mg/kg total dose over 12 days of the treatment) along with an oral administration of leucovorin as described above was within the maximum tolerated dosage, producing no treatment-related deaths in the group of ten mice within three weeks. The treatment caused a delay of two days for the quadrupling of tumor volume (from 13.3 to 15.3 days). Median tumor volume increased from 179 mm3 at treatment initiation to 1120 mm3 on Study Day 26. Co-administration of 5-FU with GM (30 mg/kg/dose), along with an oral dose of leucovorin as described above, brought further delay in tumor growth, particularly in the first half of the study: quadrupling of the tumor from 15.3 days without GM to 18.1 days with GM.

Increasing the GM dose to 120 mg/kg/dose in co-administration with 5-FU on a q4d×4 schedule along with an oral administration of leucovorin, as described above, again produced a significant delay in quadrupling of tumor volume: from 13.3 days for untreated control animals and 15.3 days for 5-FU/leucovorin-treated animals to 23.5 days for animals treated with all three drugs. Furthermore, when all three drugs were used in combination, one tumor completely disappeared four weeks after treatment initiation, two more tumors were of a relatively small size (269 and 352 mm3) by the end of the study, and three additional tumors were practically stabilized at a volume of well below 1000 mm3. Overall, median tumor volume increased from 176 mm3 at treatment initiation to only 729 mm3 at Study Day 26 (significantly less than the 1318 mm3 for untreated animals, and 1120 mm3 for 5-FU plus leucovorin-treated animals).

Example 6

Biodistribution Studies

The biodistribution of 3H-galactomannan was studied in tumor-bearing and non-tumor bearing mice. Major findings from this study indicated that tritiated galactomannan freely binds to liver, kidney, lung, tumor, and plasma. Saturation of binding did not occur at concentrations of 6 to 60 mg/kg (18 to 180 mg/m2). Tissue distribution of 3H-galactomannan was independent of the injected dose and did not change its pattern when 5-FU (342 mg/m2) was combined with 3H-galactomannan. 3H-galactomannan elimination from plasma, kidneys, lungs and tumor in the various groups was rapid, an average of approximately 50% of the one-hour radioactivity was detected at six hours except in tumor-bearing mice, where the radioactivity in tumor samples from mice treated with 6 or 60 mg/kg of 3H-galactomannan with or without 5-FU averaged approximately 72% remaining after six hours. Elimination of 3H-galactomannan from the liver was more gradual than in other tissues, and on average, more than 50% of the radioactivity detected at one hour after injection was still present at 24 hours.

Male NCr-nu athymic nude mice (Charles Rivers Laboratories, Raleigh, N.C.) were acclimated and housed as described above. The first set of animals (a total of 18 mice) were non-tumored mice. The second set of 18 mice were tumored as follows. Thirty to forty mg fragments from an in vivo passage of COLO 205 human colon tumor were implanted subcutaneously (s.c.) in mice as described above, and allowed to grow. Tumors were allowed to reach 245-392 mg in weight before the start of treatment. A sufficient number of mice were implanted so that tumors in a weight range as narrow as possible were selected for the trial on the day of treatment initiation. Those animals selected with tumors in the proper size range were divided into the various treatment groups.

Tritiation of GM from *G. triacanthos* was performed as follows. 12.8 mg of GM was dissolved in 2.0 mL of water and exposed to 25 Curies of tritium gas in the presence of Pd/BaSO4 catalyst (120 mg, totally insoluble in water). After one hour the gas supply was removed, the catalyst was filtered away, and the aqueous solution of GM was evaporated to dryness repeatedly (four-fold, adding water), until no labile tritium was found. Total yield of the labeled GM was 3.8 mCi, specific radioactivity was 300 µCi/mg.

All 36 mice, divided into 18 groups, were given a single intravenous injection of cold or tritiated GM (either 6 or 60 mg/kg) or of a combination of GM (60 mg/kg, cold or tritiated) and 5-FU (114 mg/kg) on the same day. Non-labeled GM was formulated in saline, and tritiated GM was added to the solution so that each animal received 10 µCi of radioactivity. 5-FU was dissolved in the solution containing GM (at a concentration of 6 mg/mL). All dosing solutions (100 µL each) were counted in duplicate.

Two mice per group were bled at 1, 6, and 24 hrs after injection, and plasma was prepared. Animals were then sacrificed; livers, kidneys, lungs, and tumors (from tumored animals) were collected, weighed and flash-frozen for further analysis.

After weighing, livers were dissolved in 10 mL of Soluene 350 (Packard Instruments, Downers Grove, Ill.) and incubated first for 4 hrs at 50° C., and at room temperature, until tissues were solubilized. One millilter of the resulting solution was counted in a scintillation counter as a single sample. Based on tissue weight and the sample volume, the number of µCi of tritiated GM per gram of tissue was calculated.

Kidneys were treated in the same manner, but dissolved in 2 mL of Soluene. After the tissue was solubilized at room temperature, 15 mL of Safety Solve scintillation fluid (Research Products International, Mount Prospect, Ill.) was added and samples were incubated overnight. Five mL of the resulting solution were diluted in 15 mL of Safety Solve and counted in a scintillation counter as a single sample. Lungs were treated in the same manner but dissolved in 1 mL of Soluene. Plasma samples (50 µL each) were placed direct into Safety Solve and counted as a single sample.

After weighing, tumors were dissolved in one or two milliliters of Soluene and incubated for three days at 500 C to solubilize. Fifteen milliliters of Safety Solve were then added and samples were incubated overnight at room temperature. Two milliliters of water were then added and samples were counted in a scintillation counter as a single sample.

Male NCr-nu athymic nude mice were divided into two principal sets, 18 animals in each. The first set of animals were non-tumored mice. The second set were tumored as follows. Thirty- to-forty mg fragments from an in vivo passage of COLO 205 human colon tumor were implanted subcutaneously (s.c.) in mice as described above, and allowed to grow. Tumors were allowed to reach 245-392 mg in weight before the start of treatment. A sufficient number of mice were implanted so that tumors in a weight range as narrow as possible were selected for the trial on the day of treatment initiation. Those animals selected with tumors in the proper size range were divided into the various treatment groups.

All 36 mice, divided into 18 groups, were given a single intravenous injection of cold or tritiated GM (either 6 or 60 mg/kg) or of a combination of GM (60 mg/kg, cold or tritiated) and 5-FU (114 mg/kg) on the same day. Tritiation of GM (with the resulting specific activity of 300 µCi/mg) is described above. Cold GM was formulated, in saline, and tritiated GM was added to the solution so that each animal received 10 µCi of radioactivity. 5-FU was dissolved in the solution containing GM (at a concentration of 6 mg/mL).

Two mice per group were bled at 1, 6, and 24 hrs after injection, and plasma was prepared. Animals were then sacrificed; livers, kidneys, lungs, and tumors (from tumored animals) were collected, weighed and flash-frozen for further analysis, as described above.

It was observed that the galactomannan freely binds to liver, kidney, lung, tumor, and plasma, and did not reach limits of the binding, e.g., did not reach saturation of the binding between the 6 mg/kg and 60 mg/kg doses. When 6 mg/kg (with a relative radioactivity of 1.0) and 60 mg/kg (with a relative radioactivity of 0.1) doses of the galactomannan were administered, the amount of bound radioactive galactomannan was the same; that is, the amount of bound galactomannan increased 10-fold for the 10-times higher dose.

The distribution of radioactivity in whole tissues as well as per weight or volume (in plasma) was practically identical for 6 and 60 mg/kg of GM, hence, the respective data were pooled. Also, the distribution of radioactivity in whole tissues as well as per weight or volume (in plasma) was practically identical for tumored and non-tumored animals (except in tumors, that obviously were present only in tumored animals), hence, the respective data were pooled. Overall, the data were averaged for eight animals, except the data for tumors, that are average for four animals.

The principal results of the study were as follows:

In the presence of 5-FU the amount of GM in the tumor increases, and stays increased in the course of clearance of GM; and In the presence of 5-FU the amount of GM in the liver decreases, and stays decreased in the course of clearance of GM.

That is, 5-FU and GM work in a synergism when delivered into the tumor. This might explain why GM in a combination with 5-FU increases efficacy of the drug against COLO 205 human colon tumor, bearing by mice (see above).

At the same time, 5-FU and GM work as antagonists (apparently, compete with each other for the same binding sites in the liver) when delivered into the liver.

Examples 7-9

Acute Toxicology Studies

Acute toxicology studies of the galactomannan of the present invention were performed in mice, rats and dogs and subchronic toxicology studies were performed in rats and dogs. The following is a summary of the findings of these studies:

Single IV doses of 1500 mg/m2 (336 mg/m2) of galactomannan or 417/222 mg/kg (1251/666 mg/m2) 5-FU/galactomanna produced no clinical signs of toxicity, death or decreased weight gain in mice (n=5/group), while 409 mg/kg (1227 mg/m2) 5-FU caused death in 3/5 mice after 13-16 days.

In rats (n=5/sex/group), single IV doses of 140 mg/kg (840 mg/m2) 5-FU, 72 mg/kg (432 mg/m2) galactomannan or 140/72 mg/kg of the combination produced no deaths in any of the groups. Toxic changes in body weight, feed consumption, and hematology were somewhat less severe in the rats injected with the combination, versus those injected with 5-FU alone. Galactomannan alone produced no significant untoward effects.

Single IV injections of 28.5 mg/kg (570 mg/m2) 5-FU, 15 mg/kg (300 mg/m2) of galactomannan or 28.5/15 mg/kg of 5-FU/galactomannan resulted in the death of 2/2 dogs injected with 5-FU, 2/4 dogs injected with the combination and 0/2 dogs receiving galactomannan alone. The surviving dogs remained clinically normal and had no treatment-related changes in body weight, feed consumption, ECG tracings, clinical pathology or gross tissue changes during the 21-day study period.

Example 7

Sub-Chronic Rat Study

In the 28-day subchronic rat study performed with research grade unfiltered galactomannan, single daily IV doses of 10 mL/kg saline, 48 mg/kg (288 mg/m2) 5-FU, 48 mg/kg (288 mg/m2) galactomannan or 24/13 mg/kg (144/78 mg/m2), 36/19 mg/kg (216/114 mg/m2) or 48/25 mg/kg (288/150 mg/m2) of the 5-FU/galactomannan combination were given at a rate of 1 mL/min for four consecutive days. The four doses of 5-FU produced mortality (7/8 with 48 mg/kg 5-FU; 1/8, 2/8 and 7/8 with 24/13, 36/19 and 48/25 mg/kg 5-FU/galactomannan, respectively).

Alopecia, severe transient decreases in body weight and feed consumption, and transient depression of erythrocyte parameters and platelets were observed in all groups receiving 5-FU. Lesions in unscheduled-death animals were primarily due to the expected action of 5-FU on the hematopoietic and lymphoid systems, with secondary bacterial invasion and disseminated hemorrhage due to effects on coagulation. At the study day 5 necropsy, lesions included pronounced hypocellularity of the bone marrow, lymphoid atrophy of the thymus and atrophy of villi in the various segments of the small intestine (all considered due to the expected action of 5-FU). With the exception of the mild granulomatous foci in the lungs, treatment-related histopathological lesions were resolved in animals sacrificed at study day 29 (only one female survived in Group 2 and Group 6).

Example 8

Repeat Dose Rat Study

Studies with repeat dose I.V. in rats with up to 52-day recovery period was performed using filtered GMP grade galactomannan material containing 48 or 96 mg/kg (288 or 576 mg/m2). Five animals of each sex were sacrificed at days 5, 28 and 56. The audited draft report showed that histologic findings in the lung of one rat that was sacrificed on day 5 suggested intravenous administration of galactomannan at 96 mg/kg was associated with a low incidence of trace-level granulomatous inflammation of the lung of rats that-were dosed for four consecutive days and sacrificed at day 5. Male rats given galactomanna at 96 mg/kg (a dose 2-fold greater than the highest dose used in the first study) and sacrificed on day 28 had an increased incidence of trace-level interstitial inflammation in the lungs but had no histologic evidence of granulomatous inflammation. Male rats given galactomannan at 96 mg/kg and sacrificed on day 56 had an increased incidence of trace-level alveolar macrophage accumulation but again, no histologic evidence of granulomatous inflammation.

The galactomannan of the invention has minimal histological effects with only 1/30 rats injected with 48 mg/kg dose of the GMP galactomannan clinical solution having granulomatous inflammation. None of the 30 rats injected with the 96 mg/kg dose of the GMP galactomannan clinical solution were affected. It was concluded that galactomannan clinical solutions, up to a dose of 15 mg/kg (555 mg/m2; 9 mg/mL), is safe for human use and poses no undue risk to health.

Example 9

Canine Dog Study

In a 28-day canine study, single daily IV doses of saline, 6 mg/kg (120 mg/m2) 5-FU and (500 mg/m2 (240 mg/m2) galactomannan or 4/2 mg/kg (80/40 mg/m2), 6/3.2 mg/kg (120/64 mg/m2) or 6/6 mg/kg (120/120 mg/m2) 5-FU/galactomannan were injected for four consecutive days to six groups of beagle dogs Mortality occurred in 13 of 48 dogs (five moribund sacrifices and eight found dead) between Study Days 2 and 5 (4/4 males on 5-FU; 3/4 males in the 4/2 mg/kg 5-FU/galactomannan group; 2/4 males and 1/4 females in the 6/3.2 and 6/6 mg/kg 5-FU/galactomannan groups, respectively).

Adverse effects in 5-FU groups included ataxia, prostration, vocalization, convulsions, tremors, hypersensitivity to touch, aggressive behavior (resulting in only three doses being given to the 6/3.2 5-FU/galactomanna group), emesis, salivation, soft stools and decreased red cell parameters and platelet counts. Gross/microscopic changes in unscheduled-death animals included congestion of one or more organs (suggesting cardiovascular dysfunction) and atrophy of the mucosa of the GI tract. At the day 5 necropsy, treatment-related histological changes were largely limited to the 5-FU females. At day 29 necropsy, there were no remarkable changes in the survivors. Galactomannan at 500 mg/m2 produced no observed adverse effects.

Example 10

Mutagenicity Studies

Mutagenicity studies were conducted and included two Ames bacterial reverse mutation assays in which the galactomannan of the invention was evaluated by itself in the first study and combined with 5-FU in the second study. The test articles in both studies were evaluated in bacterial assays using *Salmonella typhimurium* strains TA97a, TA98, TA100, TA1535 and *Escherichia coli* strain WP2 uvrA (pKM101), both in the presence and absence of an exogenous metabolic activation system. No evidence of mutagenic activity was detected in either of the two studies.

In summary, in vivo pharmacology studies conducted to date indicate that the galactomannan of the invention enhances the antineoplastic effects of 5-FU. The galactomannan is not mutagenic, either by itself or combined with 5-FU, in bacterial reverse mutation assays. Toxicity studies in mice, rats and dogs have shown the galactomannan to have a very low potential for toxicity and a capacity for ameliorating some of the toxic side effects of 5-FU.

Single IV doses of 112 mg/kg (336 mg/m2) of (((1,4)-linked β-D-mannopyranose)17-((1,6)-linked-β-D-galactopyranose)10)12) or 417/222 mg/kg (1251/666 mg/m2) 5-FU/(((1,4)-linked β-D-mannopyranose)17-((1,6)-linked-β-D-galactopyranose)10)12) produced no clinical signs of toxicity, death or decreased weight gain, while 409 mg/kg (1227 mg/m2) 5-FU caused death in 3/5 mice after 13-16 days.

In rats, single IV doses of 140 mg/kg (840 mg/m2) 5-FU, 7:2 mg/kg (432 mg/m2) (((1,4)-linked β-D-mannopyranose) 17-((1,6)-linked-β-D-galactopyranose)10)12) or 140/72 mg/kg of the combination produced no deaths in any of the groups. Toxic changes in body weight, feed consumption, and hematology were less severe in the rats injected with the combination, versus those injected with 5-FU alone. (((1,4)-linked β-D-mannopyranose)17-((1,6)-linked-β-D-galactopyranose)10)12) alone produced no significant untoward effects.

Example 11

Effect of Galactomannan on Chemotherapy Proteins

Cytokines and chemokines have been shown, in in vitro studies, to promote cancer cells susceptibility to destruction by the immune response. (Cytokines and chemokines are well known to those skilled in the art and a list of such can be found in any modem biology/medicine text). In few cases it has been shown that cytokines directly inhibit tumor cell growth. Cytokines function as messengers of the immune system by regulating the intensity and duration of the immune response by exerting a variety of effects on lymphocytes and other immune cells. Cytokines also control cellular proliferation and differentiation. In the USA, the Food and Drug Administration (FDA) has already approved the use of two cytokines-IL-2 and a-interferon for treatment of cancer.

It has been demonstrated that IL-2 has biological activity against renal cell disease, melanoma, lymphoma, and leukemia. Interferon has been effective against these cancers as well as against Kaposi's sarcoma, chronic myelogenous leukemia, and hairy cell leukemia.

However, there have been delivery problems and stability in the blood with deleterious side effects due to cytokine treatments. Pegilation has been used to slightly improve the pharmaceutical effectiveness of interferon, but still consider to be toxic.

The Effect of galactomannan on chemotherapy drugs has been also shown in with these proteinous chemotherapeutics, e.g., cytokine. In the following study, a combination of IL-12 (10 µg/kg) and IL-12 (40 mg/kg) alone or in combination with galactomannan (120 mg/kg) were used to treat a mice model implanted with human colon tumor HT-29. The IV injections started once tumor size reached 110 mg and were repeated 4 times at 4 days interval, the result one week after the last injection (day 26) already showed a significant improvement in inhibition of tumor growth was achieved.

What is claimed is:

1. A mixture, comprising
a first component comprising a parenteral administration vehicle,
a second component comprising a homogenous galactomannan oligosaccharide;
Wherein the homogenous galactomannan oligosaccharide has a ratio of mannose to galactose of about 1.7:1;
Wherein the homogenous galactomannan oligosaccharide consists essentially of galactose and mannose residues; and
wherein the homogenous galactomannan oligosaccharide results from a sufficiently controlled depolymerization of galactomannan so as to result in a homogenous galactomannan polysaccharide having an average molecular weight of about 4,000 to about 60,000 daltons as assayed by GPC-MALLS.

2. The formulation of claim 1, wherein said homogenous galactomannan oligosaccharide is a β-1,4-D-galactomannan.

3. The formulation of claim 2, wherein said homogenous galactomannan oligosaccharide is (((1,4)-linked β-D-mannopyranose)$_{17}$-((1,6)-linked-β-D-galactopyranose)$_{10}$)$_{12}$).

4. The formulation of claim 1, wherein the homogenous galactomannan oligosaccharide is a galectin antagonist.

5. The formulation of claim 1, wherein the homogenous galactomannan oligosaccharide is further comprised of exposed galactose residues capable of interacting with biological targets.

6. The formulation of claim 1, wherein the homogenous galactomannan oligosaccharide is further capable of interacting with regulatory sites in a biological system governed by galactose-specific residues.

7. The formulation of claim 1, wherein the parenteral administration vehicle is an oily vehicle.

8. The formulation of claim 1, wherein the parenteral administration vehicle is an aqueous vehicle.

9. The formulation of claim 1, wherein the parenteral administration vehicle further comprises formulatory agents.

10. The formulation of claim 9, wherein the formulatory agent is a suspending agent.

11. The formulation of claim 9, wherein the formulatory agent is a stabilizing agent.

12. The formulation of claim 9, wherein the formulatory agent is a dispersing agent.

* * * * *